United States Patent [19]

Wilson et al.

[11] 4,275,087
[45] Jun. 23, 1981

[54] FLAVORING WITH 2,6,6-TRIMETHYL-α-PROPENYL-1,3-CYCLOHEXADIENE-1-METHANOL SUBSTANCES

[75] Inventors: Richard A. Wilson, Westfield; William L. Schreiber, Jackson; Braja D. Mookherjee, Holmdel, all of N.J.; Jacob Kiwala, Brooklyn, N.Y.; Joaquin F. Vinals, Red Bank, N.J.; Manfred H. Vock, Locust, N.J.; Gilbert Stork, Englewood, N.J.; Frederick L. Schmitt, Holmdel, N.J.

[73] Assignee: International Flavors & Fragrances Inc., New York, N.Y.

[21] Appl. No.: 120,102

[22] Filed: Feb. 8, 1980

Related U.S. Application Data

[62] Division of Ser. No. 39,361, May 15, 1979.

[51] Int. Cl.³ .................... A23L 1/226; A23L 1/235
[52] U.S. Cl. .................................................. 426/538
[58] Field of Search ....................................... 426/538

[56] References Cited

U.S. PATENT DOCUMENTS 3,928,456 12/1975 Kovats et al. .............. 426/538 X
3,996,296 12/1976 Mookherjee et al. ........... 426/538 X

OTHER PUBLICATIONS

Raitenstrauch, Helv. Chim. Acta., 56, 2492–2507, (1973).

*Primary Examiner*—Joseph M. Golian
*Attorney, Agent, or Firm*—Arthur L. Liberman

[57] ABSTRACT

Processes and compositions are described for use in foodstuff, chewing gum, toothpaste and medicinal product flavor and aroma, smoking tobacco flavor and aroma and perfume and perfumed article aroma augmenting, enhancing and imparting compositions; and as foodstuff, chewing gum, toothpaste, medicinal product, smoking tobacco, perfume and perfumed article aroma and/or flavor imparting materials of 2,6,6-trimethyl-α-(iso)propenyl-1-cyclohexene-1-methanol and -1,3-cyclohexadiene-1-methanol derivatives or one or more of their geometric or stereoisomers as defined by the generic structure:

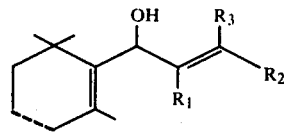

wherein one of $R_1$, $R_2$ or $R_3$ is methyl and the other two of $R_1$, $R_2$ and $R_3$ represents hydrogen; the dashed line is a carbon-carbon double bond or a carbon-carbon single bond; with the proviso that when $R_1$ is hydrogen, the dashed line is a carbon-carbon double bond.

2 Claims, 12 Drawing Figures

GLC PROFILE FOR EXAMPLE I.

NMR SPECTRUM FOR EXAMPLE I.

IR SPECTRUM FOR EXAMPLE I.

GLC PROFILE FOR EXAMPLE XI.
"CIS" ISOMER.
"TRANS" ISOMER

NMR SPECTRUM FOR EXAMPLE XI, MIXTURE OF CIS & TRANS ISOMERS.

IR SPECTRUM FOR EXAMPLE XI, CIS & TRANS ISOMER MIXTURE. (70:30; TRANS:CIS)

N M R SPECTRUM FOR EXAMPLES XI & XII, "CIS" ISOMER

N M R SPECTRUM FOR EXAMPLES XI & XII, "TRANS" ISOMER.

IR SPECTRUM FOR EXAMPLES XI & XII, TRANS ISOMER

GLC PROFILE FOR EXAMPLE XVII.

NMR SPECTRUM FOR EXAMPLE XVII.

IR SPECTRUM FOR EXAMPLE XVII.

FLAVORING WITH 2,6,6-TRIMETHYL-α-PROPENYL-1,3-CYCLOHEXADIENE-1-METHANOL SUBSTANCES

This is a divisional of application Ser. No. 039,361, filed May 15, 1979.

BACKGROUND OF THE INVENTION

The present invention relates to 2,6,6-trimethyl-α-(iso)propenyl-1-cyclohexene-1-methanols and -1,3-cyclohexadiene-1-methanols having the generic structure:

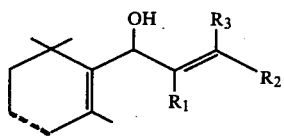

wherein one of $R_1$, $R_2$ or $R_3$ is methyl and the other two of $R_1$, $R_2$ and $R_3$ represents hydrogen; wherein the dashed line represents a carbon-carbon double bond or a carbon-carbon single bond with the proviso that when $R_1$ is hydrogen, the dashed line represents a carbon-carbon double bond and geometric and stereoisomers thereof having the specific structures:

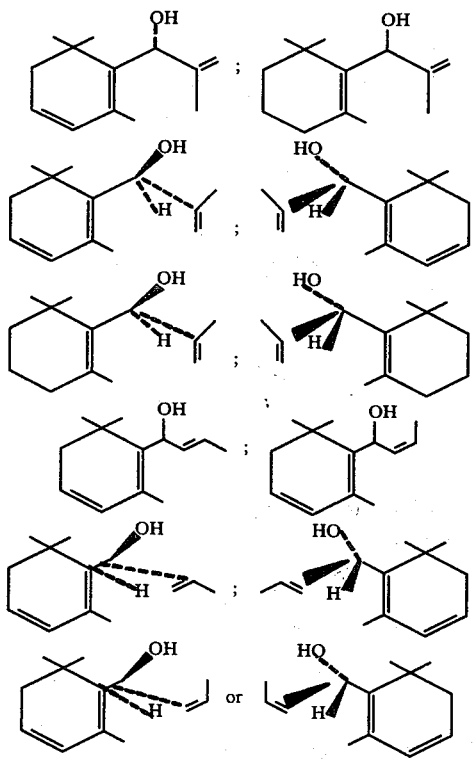

produced by the process of our invention and novel compositions using one or more of such isomers of 2,6,6-trimethyl-α-(iso)propenyl-1-cyclohexene-1-methanols and -1,3-cyclohexadiene-1-methanols to augment or enhance the flavor and/or aroma of consumable materials or to impart flavor and/or aroma to consumable materials.

There has been considerable work performed relating to substances which can be used to impart (modify, augment or enhance) flavors and/or fragrances to (or in) various consumable materials including foodstuffs, chewing gums, toothpastes, medicinal products, perfumes, perfumed articles and smoking tobaccos. These substances are used to diminish the use of natural materials, some of which may be in short supply and to provide more uniform properties in the finished product.

Sweet, camphoraceous, damascenone-like, raspberry-like, raspberry juice-like, rosey, woody/ionone-like, oriental, tobacco-like, tea-like, grape-like, fruity and ionone-like aroma and flavor notes are particularly desirable for many uses in foodstuff, chewing gum, toothpaste, and medicinal product flavorings and in foodstuffs, chewing gums, toothpastes and medicinal products, per se.

Sweet, musty, hay-tobacco-like, fruity-raspberry, ionone-like aroma characteristics prior to smoking and fruity-tobacco-like, Virginia tobacco-like nuances on smoking in the main stream and in the side stream are particularly desirable for many uses in smoking tobacco flavorings and in smoking tobaccos per se.

Leathery, hay, woody, mustard, minty, spicey (clove) and pulegone-like aromas with hay/tobacco and honey ionone-like topnotes and with safranal-like nuances are desirable in several types of perfumed compositions, perfumed articles (e.g., fabric softener materials, detergents (anionic, cationic and nonionic) and soaps) and colognes.

Hydroxy alkenyl cyclohexenes are known in the perfumery and flavor arts as disclosed by Swiss Pat. Nos. 536,834 and 557,422. Thus, Swiss Pat. No. 536,834 sets forth the reaction sequence:

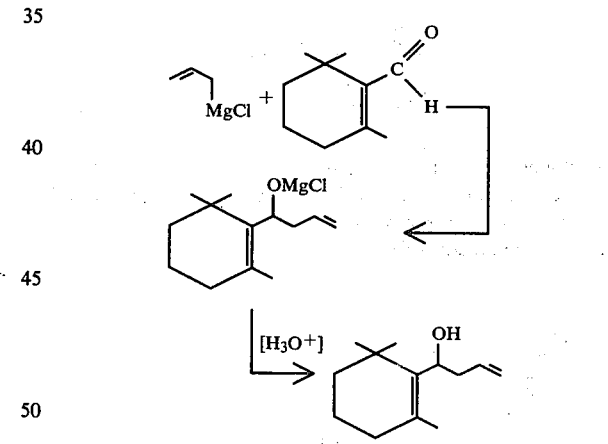

producing a compound useful for its organoleptic properties. By the same token, Swiss Pat. No. 557,422 discloses production of a compound having the structure:

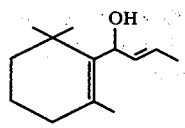

None of the compounds of Swiss Pat. Nos. 536,834 or 557,422 have properties bearing any relationship to the properties of 2,6,6-trimethyl-α-(iso)propenyl-1-cyclohexene-1-methanols and -1,3-cyclohexadiene-1-methanols of the instant application.

The 2,6,6-trimethyl-α-(iso)propenyl-1-cyclohexene-1-methanols and -1,3-cyclohexadiene-1-methanols of our invention and their stereoisomers and geometric isomers have unexpected, unobvious and advantageous organoleptic properties insofar as their organoleptic properties are concerned when compared with the pertinent prior art compounds.

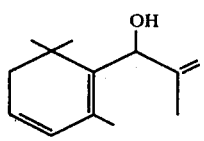

Figure 2:
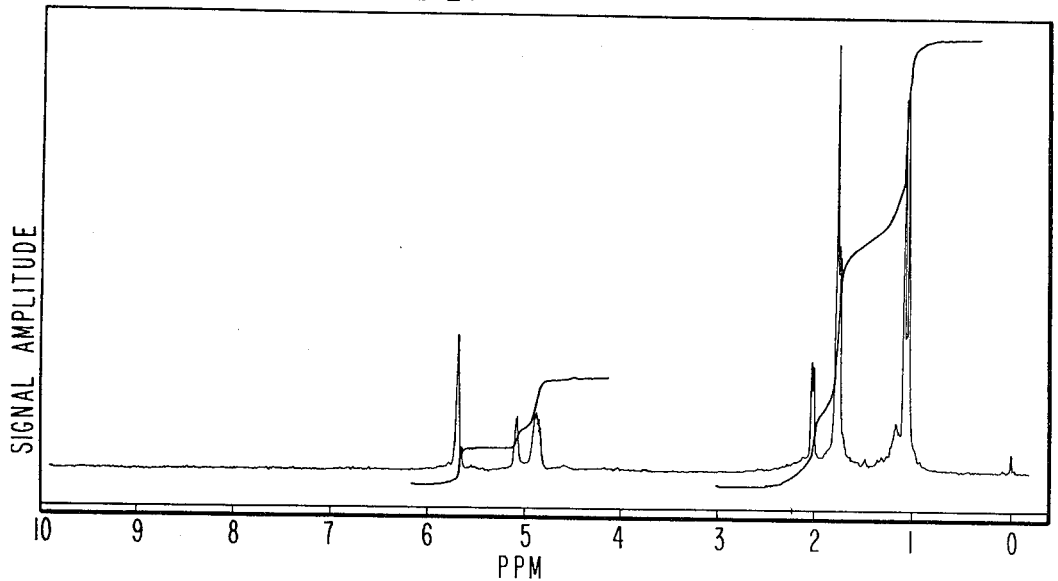

FIG. 2 is the NMR spectrum for the compound having the structure

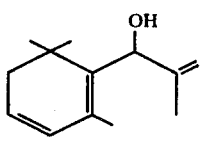

produced according to Example I.

Figures 3, 4:
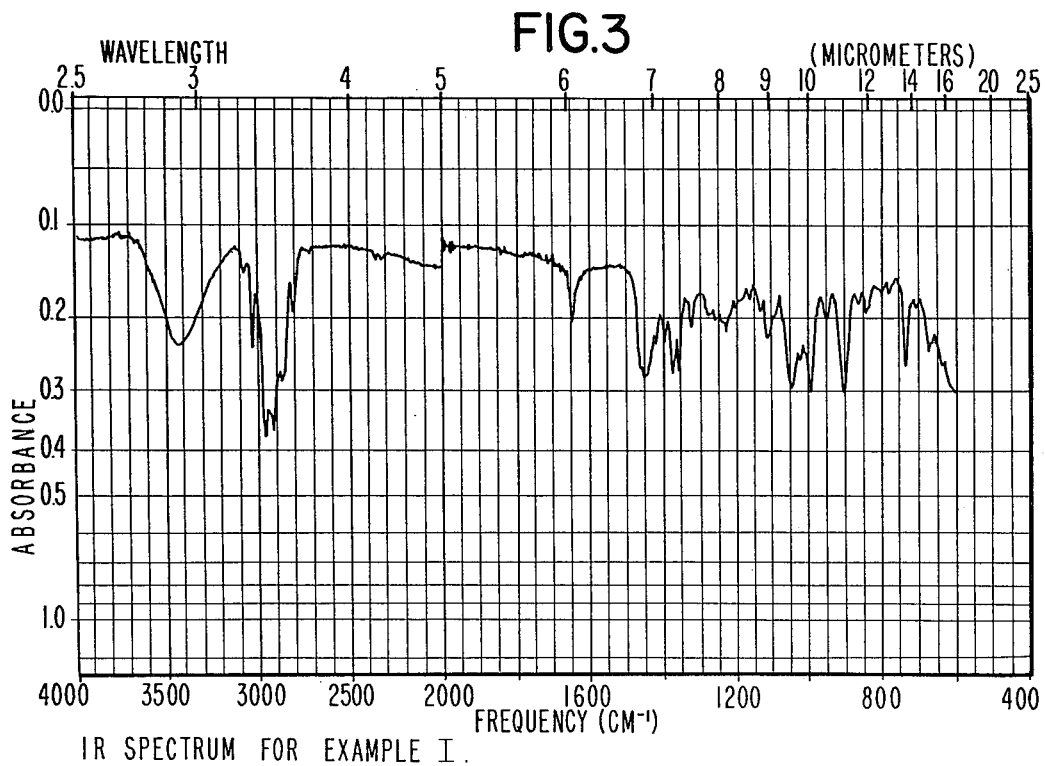

FIG. 3 is the infrared spectrum for the compound having the structure:

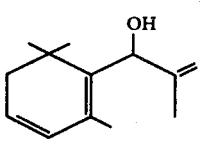

produced according to Example I.

FIG. 4 is the GLC profile for the reaction product of Example XI consisting essentially of the compounds having the structures:

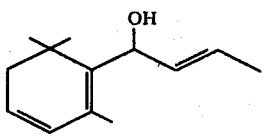

and

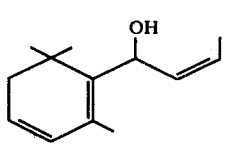

Figure 5:
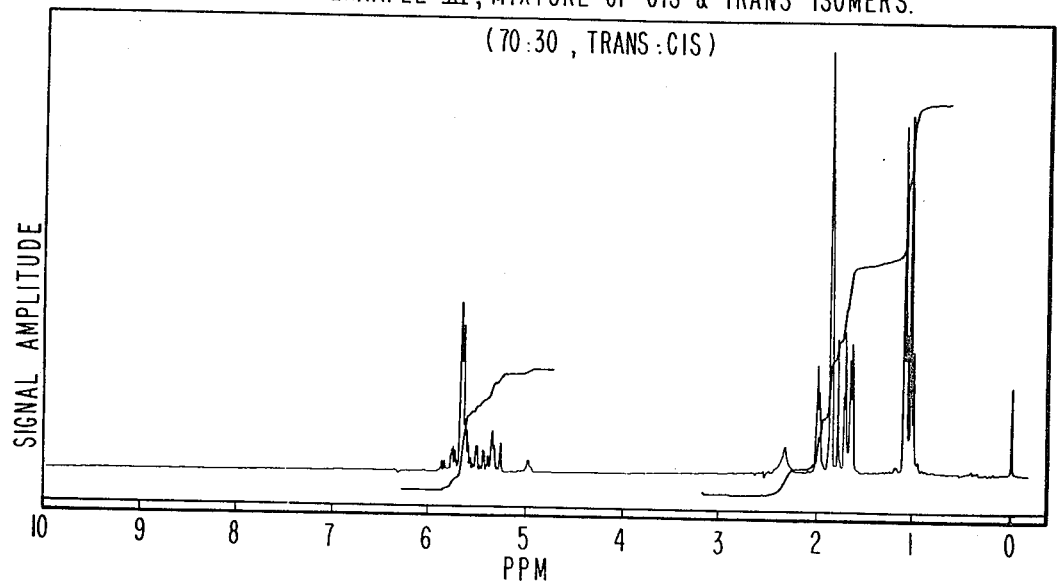

FIG. 5 is the NMR spectrum for the mixture of trans and cis isomers (70:30 trans:cis ratio) of the compounds having the structures:

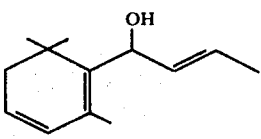

and

produced according to Example XI.

Figure 6:
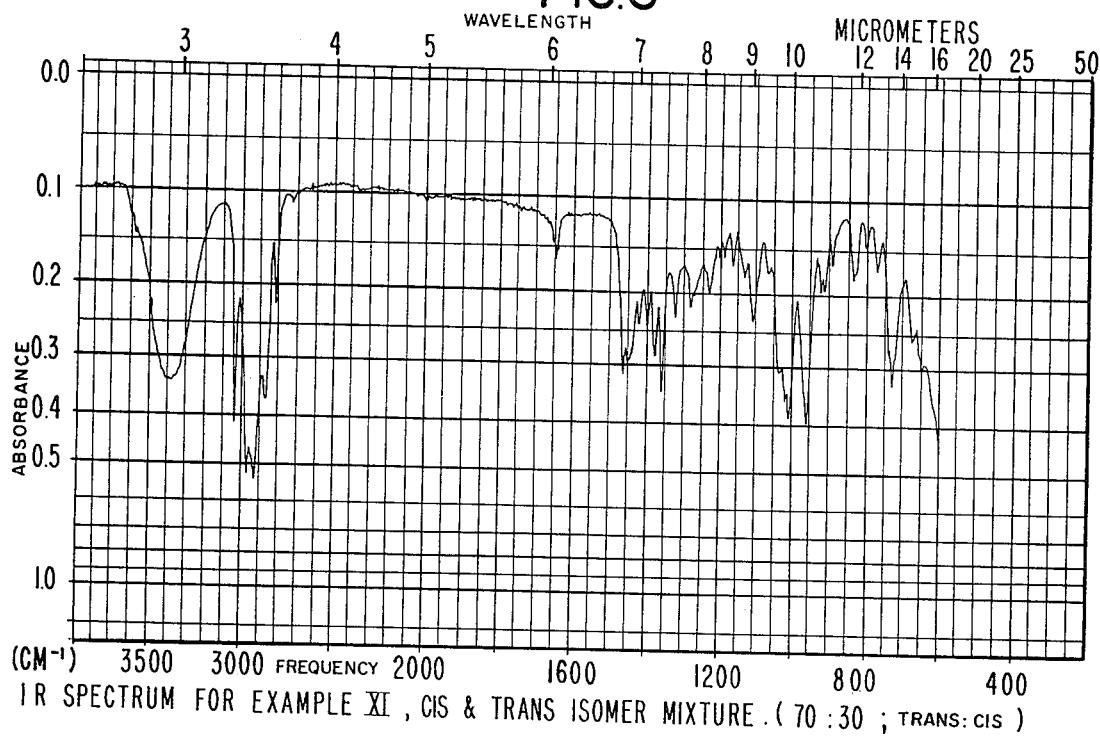

FIG. 6 is the infrared spectrum for the mixture of trans and cis compounds (70:30 trans:cis ratio) having the structures:

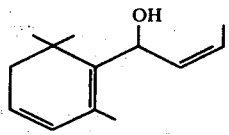

and

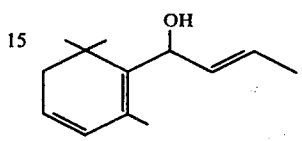

produced according to Example XI.

Figure 7:
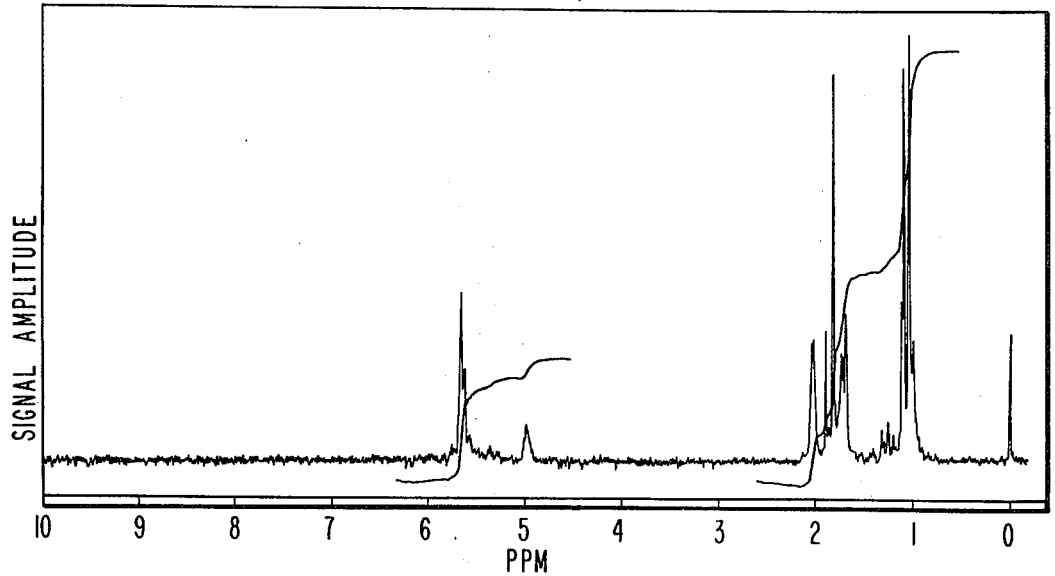

FIG. 7 is the NMR spectrum for the cis isomer of the product produced according to Example XI having the structure:

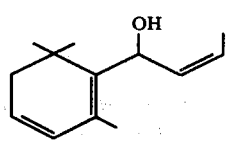

Figure 8:
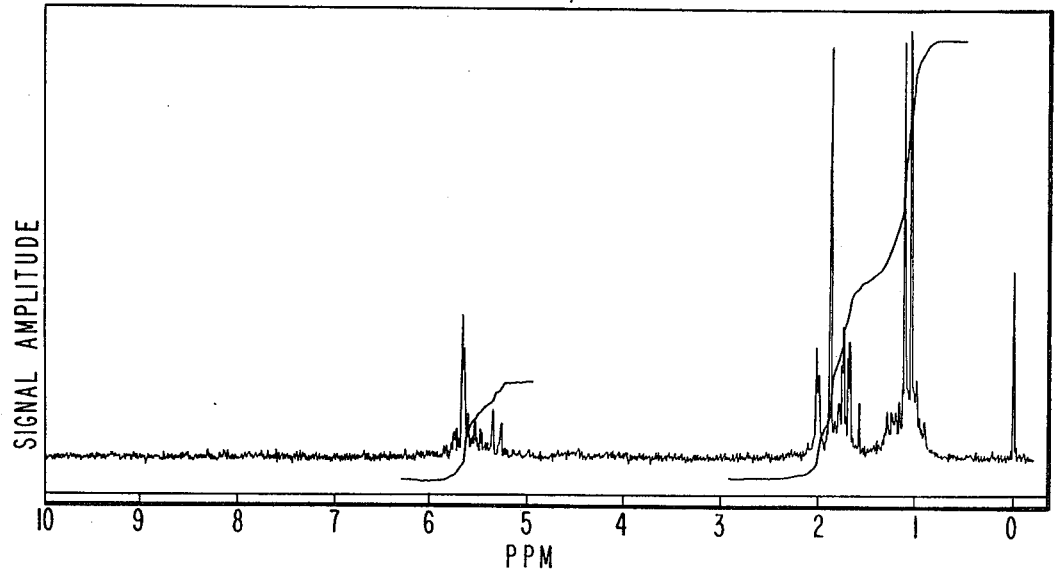

FIG. 8 is the NMR spectrum for the trans isomer of the product produced according to Example XI having the structure:

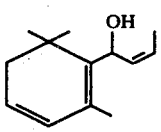

Figure 9:
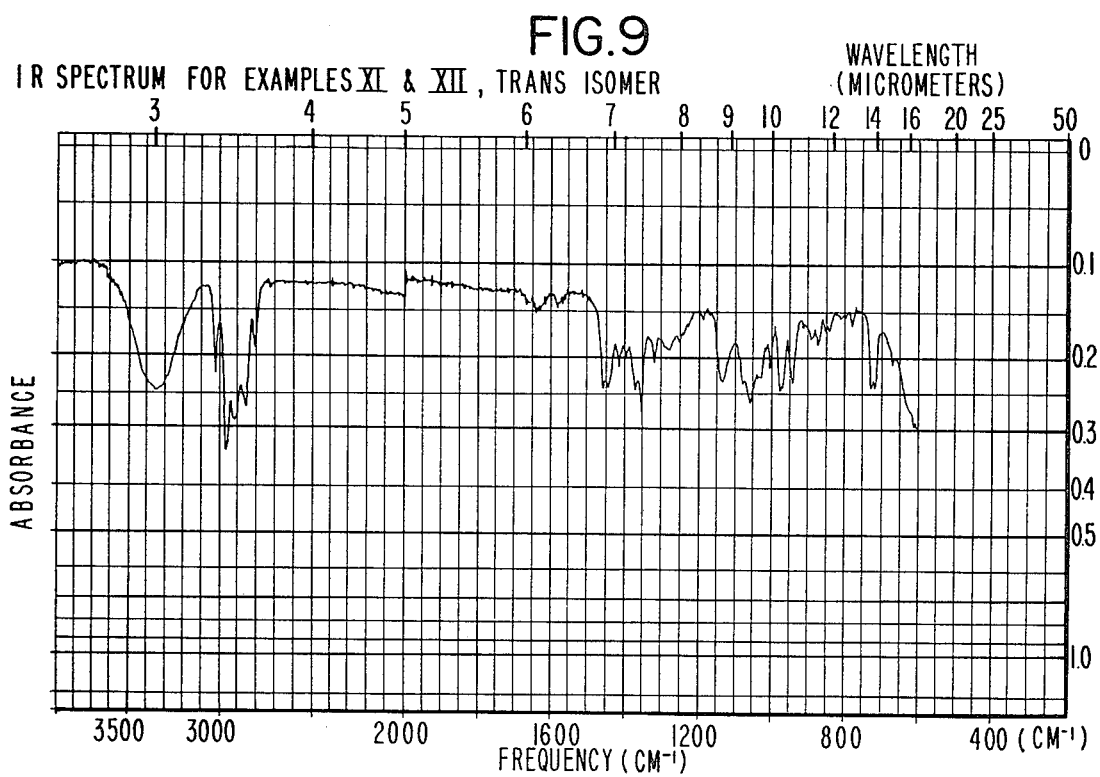

FIG. 9 is the infrared spectrum for the trans isomer of the compound having the structure:

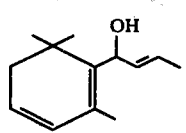

produced according to Example XI.

Figure 10:
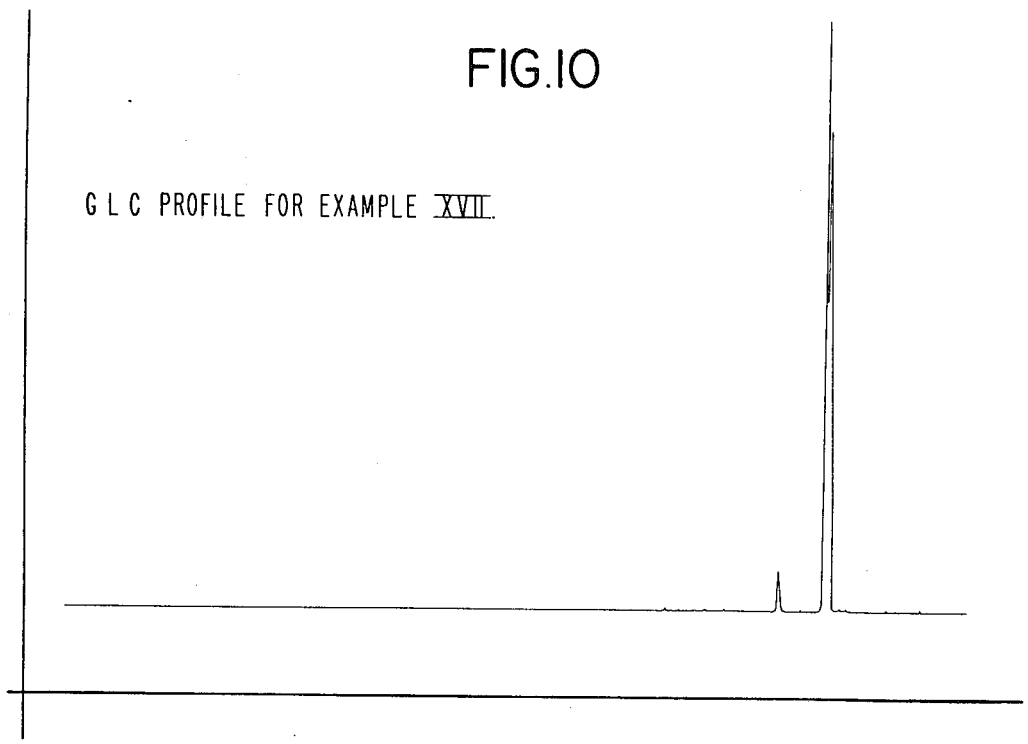

FIG. 10 is the GLC profile for the reaction product produced according to Example XVII consisting essentially of the compound having the structure:

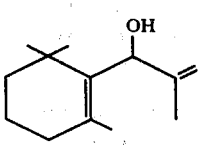

Figure 11:
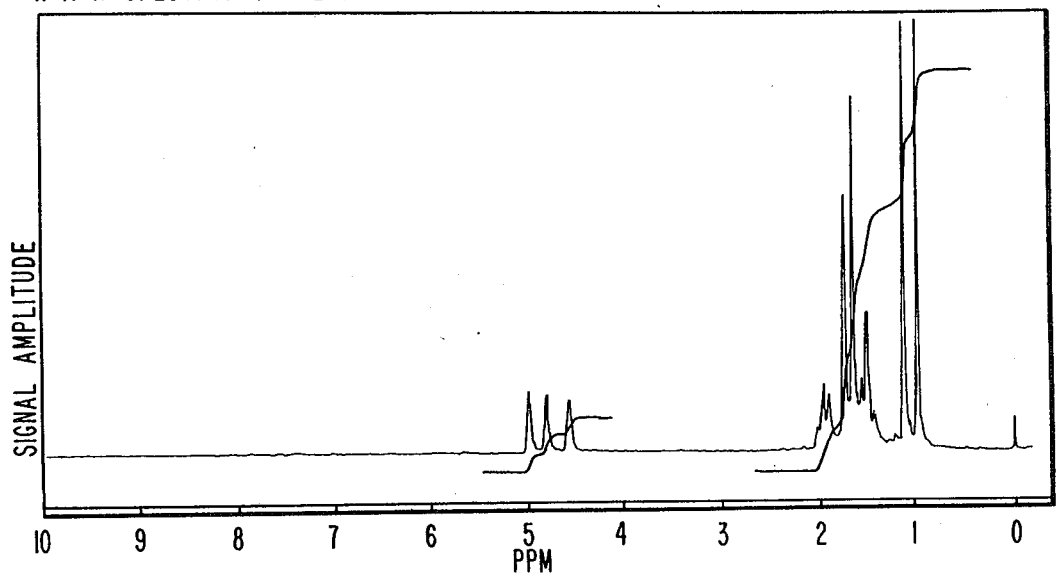

FIG. 11 is the NMR spectrum for the product produced according to Example XVII having the structure:

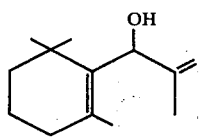

Figure 12:
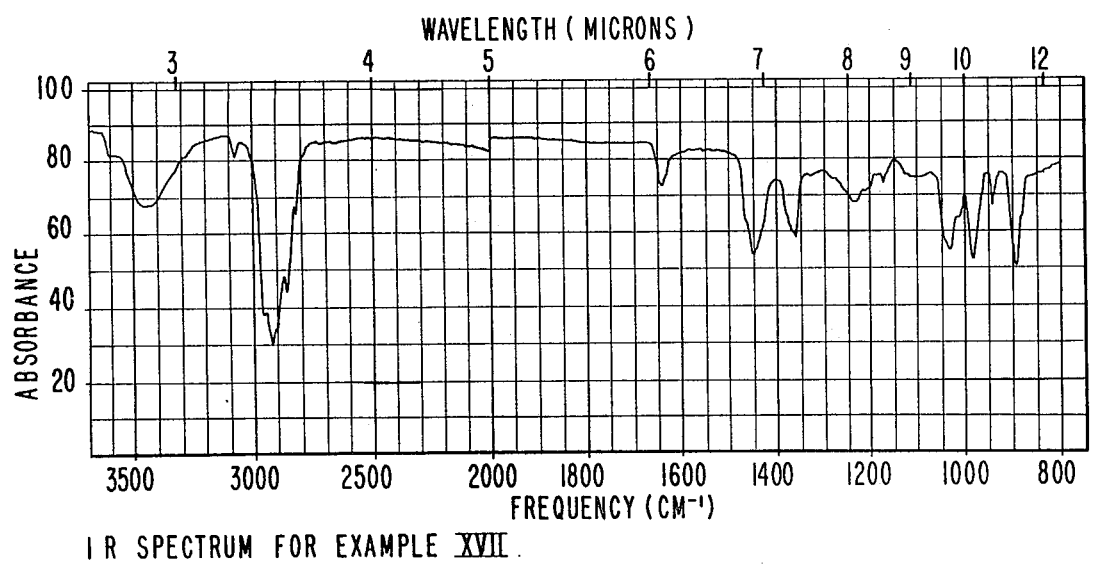

FIG. 12 is the infrared spectrum for the compound having the structure:

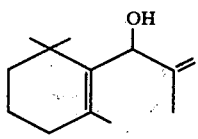

produced according to Example XVII.

THE INVENTION

It has now been discovered that novel solid and liquid perfume compositions, colognes and perfumed articles having leathery, hay, woody, mustard, minty, spicey (clove) and pulegone-like aromas with hay/tobacco and honey-ionone-like topnotes and safranal-like nuances and novel smoking tobacco and smoking tobacco flavor compositions having sweet-musty, hay-tobacco-like, fruity-raspberry, ionone-like aromas prior to smoking and fruity-tobacco-like, Virginia tobacco-like aromas and tastes on smoking in the main stream and in the side stream and novel solid and liquid flavoring compositions for foodstuffs, chewing gums, toothpastes and medicinal products (e.g., cough syrups) having sweet, camphoraceous, damascenone-like, raspberry-like, raspberry juice-like, tea-like, grape-like, fruity and ionone-like aromas and tastes useable for raspberry flavors, raspberry juice flavors and grape flavors may be provided by utilization of one or more 2,6,6-trimethyl-α-(iso)propenyl-1-cyclohexene-1-methanols and -1,3-cyclohexadiene-1-methanols or one or more of their geometric isomers or stereoisomers defined by the generic structure:

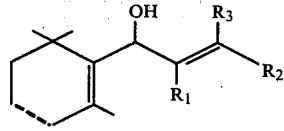

wherein one of $R_1$, $R_2$ or $R_3$ is methyl and the other two of $R_1$, $R_2$ and $R_3$ is hydrogen; wherein the dashed line represents a carbon-carbon double bond or a carbon-carbon single bond; with the proviso that when $R_1$ is hydrogen, then the dashed line represents a carbon-carbon double bond, having specifically one of the structures:

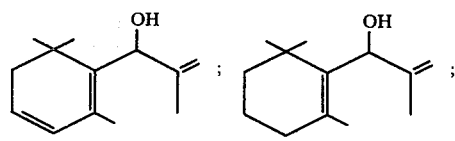

-continued

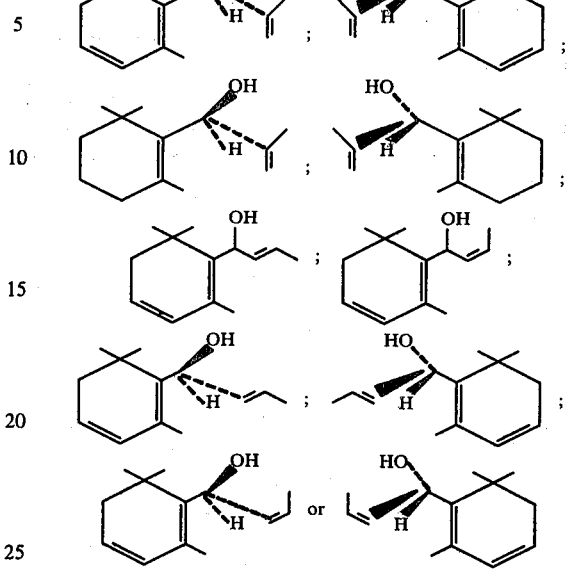

in foodstuffs, chewing gums, toothpastes, medicinal products, perfumes, colognes, perfumed articles (e.g., soaps, anionic detergents, cationic detergents, and nonionic detergents or fabric softener compositions), smoking tobaccos and smoking tobacco flavoring compositions.

The 2,6,6-trimethyl-α-(iso)propenyl-1-cyclohexene-1-methanols and -1,3-cyclohexadiene-1-methanols and stereoisomers and geometric isomers thereof may be produced according to a procedure whereby n-propenyl lithium or iso-propenyl lithium is reacted with 2,6,6-trimethyl-1-cyclohexene-1-carboxaldehyde or with 2,6,6-trimethyl-1,3-cyclohexadiene carboxaldehyde in anhydrous media in order to produce an organolithium salt. The organolithium salt is then hydrolyzed in an acidic medium to produce the 2,6,6-trimethyl-α-(iso)-propenyl-1-cyclohexene-1-methanols and -1,3-cyclohexadiene-1-methanols according to the reaction sequence:

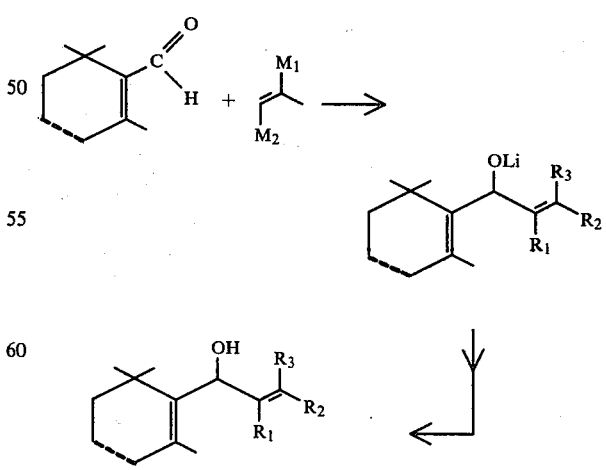

wherein one of $R_1$, $R_2$ or $R_3$ is methyl and the other two of $R_1$, $R_2$ and $R_3$ is hydrogen; the dashed line represents a carbon-carbon double bond or a carbon-carbon single bond with the proviso that when $R_1$ is hydrogen, the dashed line represents a carbon-carbon double bond; wherein one of $M_1$ or $M_2$ is lithium and the other of $M_1$ and $M_2$ is hydrogen. More specifically, the 2,6,6-trimethyl-α-isopropenyl-1-cyclohexene-1-methanols and -1,3-cyclohexadiene-1-methanols of our invention may be produced using 2-propenyl lithium and "safranal" (2,6,6-trimethyl-1,3-cyclohexadiene-1-carboxaldehyde) or dihydro safranal (2,6,6-trimethyl-1-cyclohexene-1-carboxaldehyde) as starting materials according to the reaction sequence:

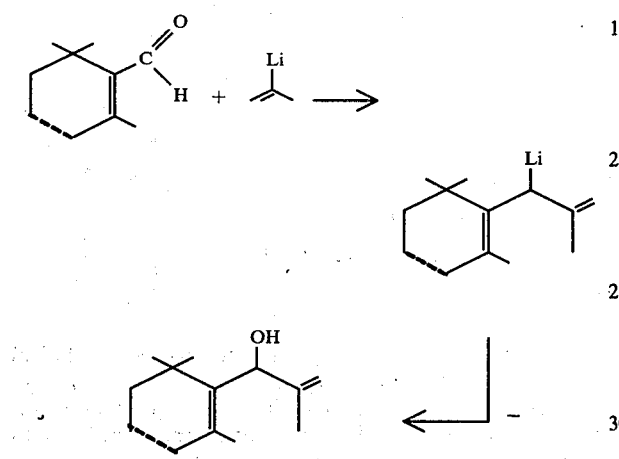

wherein the dashed line is a carbon-carbon double bond or a carbon-carbon single bond.

The reaction with the alkenyl lithium and the safranal derivative takes place in anhydrous medium in the presence of an inert solvent such as anhydrous diethyl ether or tetrahydrofuran. The mole ratio of the safranal derivative:isopropenyl lithium is about 1:1 with the isopropenyl lithium being in slight excess, preferably. The isopropenyl lithium is preferably also formed in situ from, for example, 2-bromo-1-propene and lithium wire in the presence of diethyl ether or tetrahydrofuran. After the lithium salt is formed, it is hydrolyzed in an acidic medium such as saturated aqueous ammonium chloride solution. The resulting product is then separated from the solvent and from the rest of the reaction mass by such techniques as fractional distillation.

Stereoisomers exist of the resulting compounds and these stereoisomers may be separated by standard stereoisomer separation techniques, that is, for example, in the instant case, by esterification of the resulting racemic mixture with d-lactic acid ethyl ester and subsequent chromatographic separations or separation by means of fractional crystallization of the resulting dd- and dl- stereoisomers.

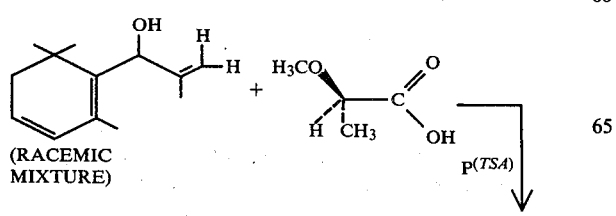

(RACEMIC MIXTURE)

p(TSA)

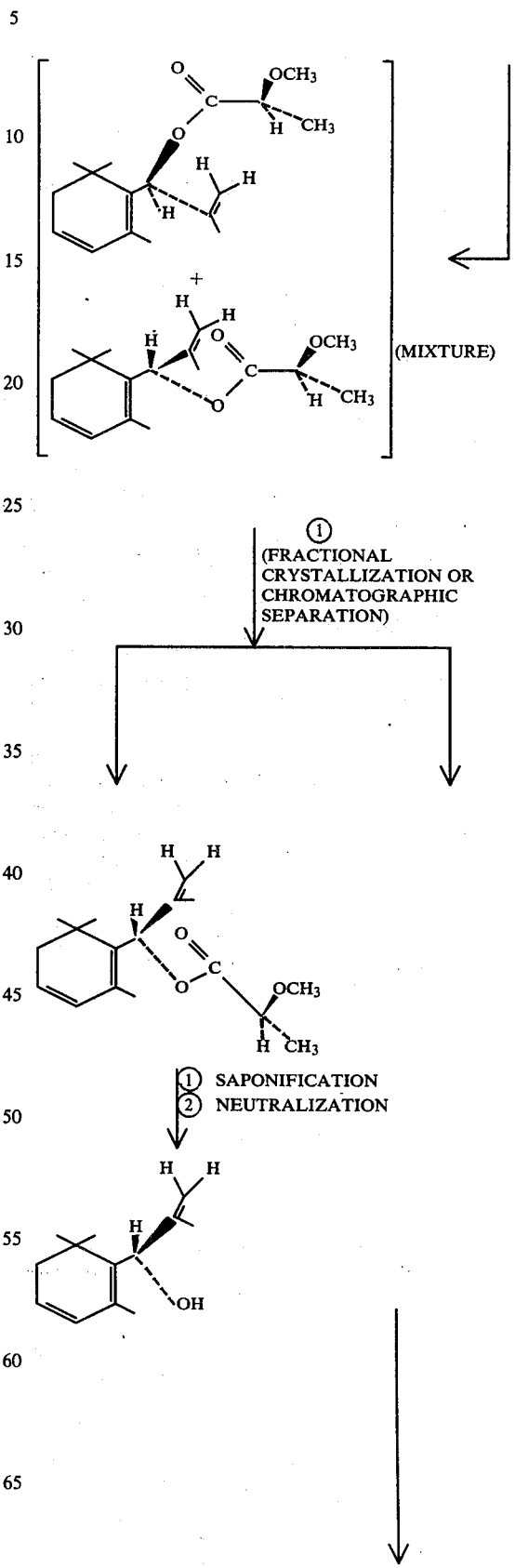

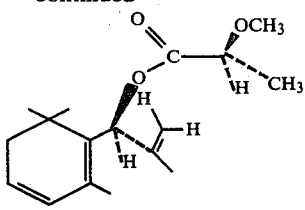

① SAPONIFICATION
② NEUTRALIZATION

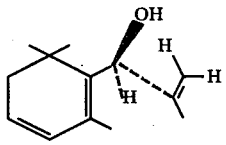

The 2,6,6-trimethyl-α-n-propenyl-1-cyclohexenemethanols and -1,3-cyclohexadiene-1-methanols and stereoisomers and geometric isomers may also be produced according to a procedure similar to that set forth in Swiss Pat. No. 536,834 with the exception that instead of an allyl Grignard reagent being reacted with 2,6,6-trimethyl-cyclohex-1-ene carboxaldehyde, a 1-propenyl Grignard reagent is reacted with 2,6,6-trimethyl-1,3-cyclohexadiene-1-carboxaldehyde according to the reaction sequence:

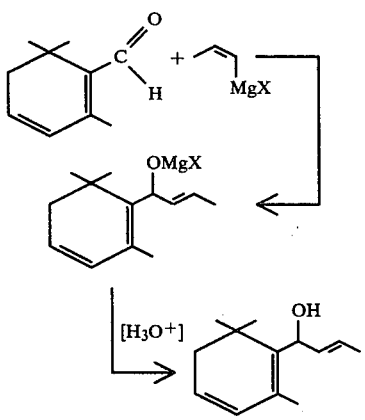

wherein X is one of chloro, iodo or bromo. More specifically and preferably the 2,6,6-trimethyl-α-propenyl-1-cyclohexene-1-methanols and -1,3-cyclohexadiene-1-methanols of our invention as produced using 1-propenyl-magnesium bromide and "safranal" (2,6,6-trimethyl-1,3-cyclohexadiene-1-carboxaldehyde) or "dihydro safranal" (2,6,6-trimethyl-1-cyclohexene-1-carboxaldehyde) as starting materials as illustrated by the reaction sequence:

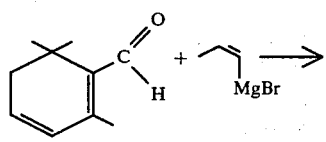

wherein, depending upon whether or not the "cis" or "trans" 1-propenyl magnesium bromide is used as a starting material, the resulting 2,6,6-trimethyl-α-propenyl-cyclohexene-1-methanols and -1,3-cyclohexadiene-1-methanols produced are "cis" or "trans" or a mixture of "cis" and "trans" geometric isomers. The stereoisomers (or "enantiomers") of these "cis" and "trans" isomers may be separated by standard stereoisomer separation techniques; that is, for example, in the instant case, by esterification of the resulting racemic mixture of 2,6,6-trimethyl-α-propenyl-1-cyclohexene-1-methanols and -1,3-cyclohexadiene-1-methanols ("cis" or "trans" isomers or mixtures of "cis" or "trans" isomers of 2,6,6-trimethyl-α-propenyl-1-cyclohexene-1-methanols and -1,3-cyclohexadiene-1-methanols) with d-lactic acid ethyl ether illustrated by the reaction sequence:

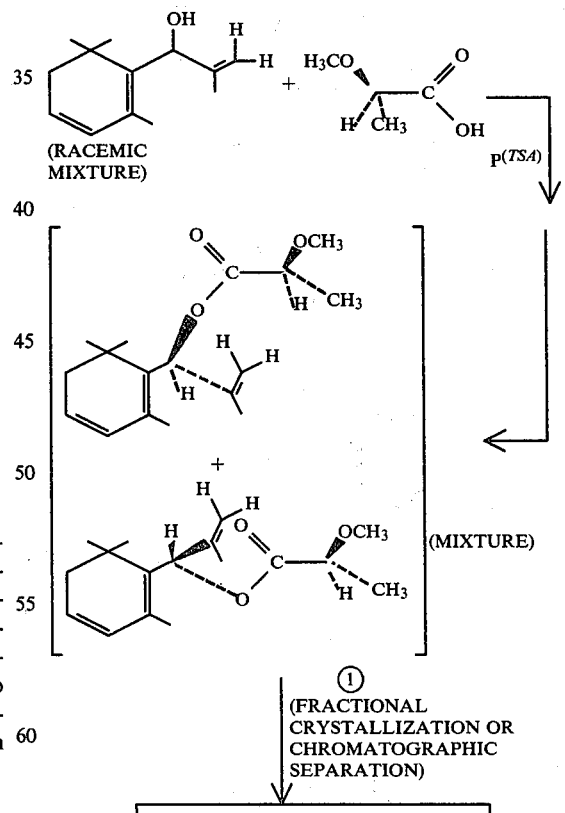

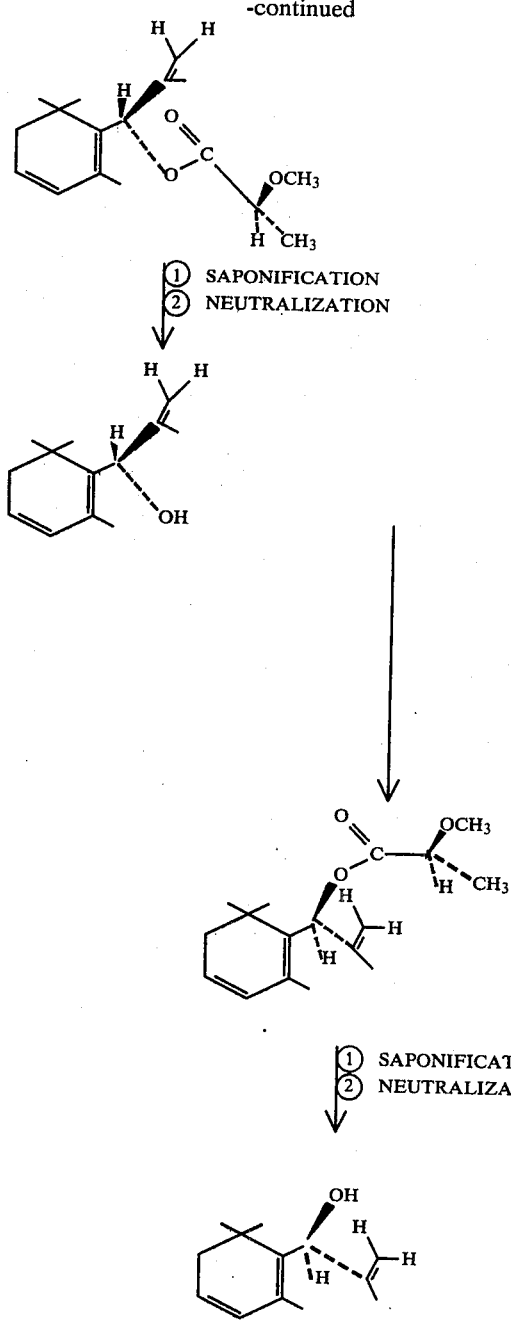

-continued

The resulting "dl" and "dd" isomers (esters) are then separated by means of column chromatography and the resulting "dl" and "dd" separate isomers are then individually saponified to yield the stereoisomers having the structures:

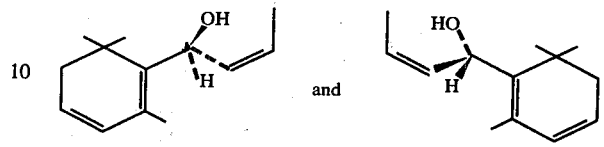

or in the case of the isopropenyl derivatives having the structures:

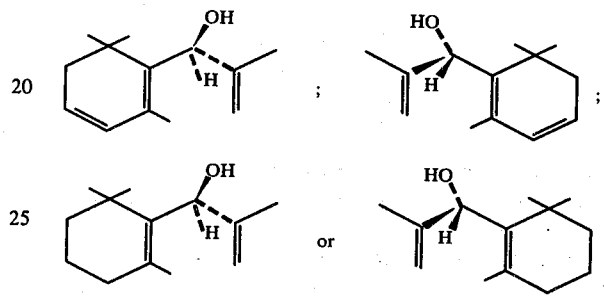

The samples of the products produced according to the processes of our invention and their organoleptic properties are as follows:

| Structure of Products | Perfumery Properties | Food Flavor Affecting Properties | Tobacco Flavor Affecting Properties |
|---|---|---|---|
| (structure with OH) | Leathery, developing a minty pulegone-like note with hay-tobacco notes. | Sweet, rosey, damascenone-like, raspberry juice-like, tea, grape-like, tobacco-like aroma and flavor characteristics at 1 ppm. | Prior to smoking, a sweet, hay-like, tobacco-like and musty aroma. On smoking, a Virginia-like flavor with additional sweet nuances in the main stream and the side stream. |

| Structure of Products | Perfumery Properties | Food Flavor Affecting Properties | Tobacco Flavor Affecting Properties |
|---|---|---|---|
| ![OH structure] | | A sweet, camphoraceous, damascenore-like, raspberry-like, rosey, woody/ionone, oriental, tobacco aroma and flavor characteristic useful for raspberry-like and tobacco-like flavor at 2 ppm. | Prior to smoking, a sweet, woody musty aroma and on smoking, Virginia-like, sweet, bitter musty aroma nuances in the main stream and in the side stream. |
| Mixture of: ![OH structure] and ![OH structure] | | A sweet, fruity, raspberry-like, damascenone-like, ionone aroma and taste. | Prior to smoking, a sweet, woody, fruity, slightly hay, slightly musty tobacco-like aroma. On smoking, a Virginia tobacco-like, woody, sweet aroma and taste with bitter and astringent nuances in the main stream and in the side stream. |

In general, the processes for preparing the compounds of our invention can be described by the following generic process:

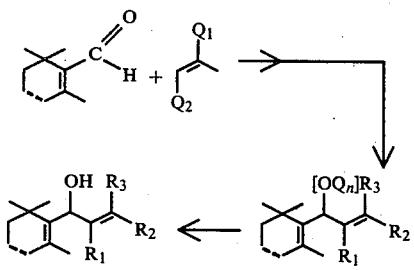

wherein one of $R_1$, $R_2$ or $R_3$ is methyl and the other two of $R_1$, $R_2$ and $R_3$ represent hydrogen; the dashed line represents a carbon-carbon double bond or a carbon-carbon single bond; with the proviso that when $R_1$ is hydrogen, the dashed line represents a carbon-carbon double bond wherein $Q_n$ represents $Q_1$ or $Q_2$; and one of $Q_1$ or $Q_2$ is Li or MgX and the other of $Q_1$ or $Q_2$ is hydrogen; and X represents chloro, bromo or iodo.

When the 2,6,6-trimethyl-α-(iso)propenyl-1-cyclohexene-1-methanols and -1,3-cyclohexadiene-1-methanols of our invention are used as food flavor adjuvants, the nature of the coingredients included with the 2,6,6-trimethyl-α-(iso)propenyl-1-cyclohexene-1-methanols and -1,3-cyclohexadiene-1-methanols of our invention used in formulating the product composition will also serve to alter, modify, augment or enhance the organoleptic characteristics of the ultimate foodstuff treated therewith.

As used herein in regard to flavors, the terms "alter", "modify" and "augment" in their various forms means "supplying or imparting flavor character or note to otherwise bland, relatively tasteless substances or augmenting the existing flavor characteristic where a natural flavor is deficient in some regard or supplementing the existing flavor impression to modify its quality, character or taste".

The term "enhance" is used herein to mean the intensification of a flavor or aroma characteristic or note without the modification of the quality thereof. Thus, "enhancement" of a flavor or aroma means the enhancement agent does not add any additional flavor note.

As used herein, the term "foodstuff" includes both solid and liquid ingestible materials which usually do, but need not, have nutritional value. Thus, foodstuffs include soups, convenience foods, beverages, dairy products, candies, chewing gums, vegetables, cereals, soft drinks, snacks and the like.

As used herein, the term "medicinal product" includes both solids and liquids which are ingestible non-toxic materials which have medicinal value such as cough syrups, cough drops, aspirin and chewable medicinal tablets.

The term "chewing gum" is intended to mean a composition which comprises a substantially water-insoluble, chewable plastic gum base such as chicle, or substitutes therefor, including jelutong, guttakay rubber or certain comestible natural or synthetic resins or waxes. Incorporated with the gum base in admixture therewith may be plasticizers or softening agents, e.g., glycerine; and a flavoring composition which incorporates the 2,6,6-trimethyl-α-(iso)propenyl-1-cyclohexene-1-methanols and -1,3-cyclohexadiene-1-methanols of our invention, and in addition, sweetening agents which may be sugars, including sucrose or dextrose and/or artificial sweeteners such as cyclamates or saccharin. Other optional ingredients may also be present.

Substances suitable for use herein as co-ingredients of flavoring adjuvants are well known in the art for such use, being extensively described in the relevant literature. It is a requirement that any such material be "ingestibly" acceptable and thus non-toxic and otherwise non-deleterious particularly from an organoleptic standpoint whereby the ultimate flavor and/or aroma of the consumable material used is not caused to have unacceptable aroma and taste nuances. Such materials may in general be characterized as flavoring adjuvants or vehicles broadly comprising stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxy-anisole (mixture of 2- and 3-tertiary-butyl-4-hydroxy anisole), butylated hydroxy toluene (2,6-di-tertiary-butyl-4- methyl phenol), propyl gallate and the like and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth, gelatin, proteinaceous materials; lipids; carbohydrates; starches, pectins and emulsifiers, e.g., mono- and diglycerides of fatty acids, skim milk powder, hexoses, pentoses, disaccharides, e.g., sucrose, corn syrup an the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, 2-methyl-2-pentenoic acid and 2-methyl-3-pentenoic acid; ketones and aldehydes, e.g., acetaldehyde, acetophenone, acetone, acetyl methyl carbinol, acrolein, n-butanal, crotonal, diacetyl, 2-methyl butanal, beta, beta-dimethyl-acrolein, methyl-n-amyl ketone, n-hexanal, 2-hexenal, iso-pentanal, hydrocinnamic aldehyde, cis-3-hexenal, 2-heptenal, nonyl aldehyde, 4-(p-hydroxyphenyl)-2-butanone, alpha-ionone, beta-ionone, 2-methyl-3-butanone, benzaldehyde, β-damascone, β-damascenone, acetophenone, 2-heptanone, o-hydroxyacetophenone, 6-methyl-5-hepten-2-one, 2-octanone, 2-undecanone, 3-phenyl-4-pentenal, 2-phenyl-2-hexenal, 2-phenyl-2-pentenal, furfural, 5-methyl furfural, cinnamaldehyde, beta-homocyclocitral, 2-pentanone, 2-pentenal and propanal; alcohols such as 1-butanol, benzyl alcohol, 1-borneol, trans-2-buten-1-ol, ethanol, geraniol, 1-hexanol, 2-heptanol, trans-2-hexenol-1, cis-3-hexen-1-ol, 3-methyl-3-buten-1-ol, 1-pentanol, 1-penten-3-ol, p-hydroxyphenyl-2-ethanol, isoamyl alcohol, isofenchyl alcohol, phenyl-2-ethanol, alpha-terpineol, cis-terpineol hydrate, eugenol, linalool, 2-heptenol-1, acetoin; esters, such as butyl acetate, ethyl acetate, ethyl acetoacetate, ethyl benzoate, ethyl butyrate, ethyl caprate, ethyl caproate, ethyl caprylate, ethyl cinnamate, ethyl crotonate, ethyl formate, ethyl isobutyrate, ethyl isovalerate, ethyl laurate, ethyl myristate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, alpha-methylphenylglycidate, ethyl succinate, isobutyl cinnamate, cinnamyl formate, methyl cinnamate, the methyl, ethyl and isobutyl esters of 2-methyl-2-pentenoic acid and 2-methyl-cis-3-pentenoic acid and terpenyl acetate; hydrocarbons such as dimethyl naphthalene, dodecane, methyl diphenyl, methyl naphthalene, myrcene, naphthalene, octadecane, tetradecane, tetramethyl naphthalene, tridecane, trimethyl naphthalene, undecane, caryophyllene, 1-phellandrene, p-cymene, 1-alpha-pinene; pyrazines such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, 2-isopropyl-3,5-dimethylpyrazine, 2-methyl-5-ethylpyrazine, tetramethylpyrazine, trimethylpyrazine; essential oils, such as jasmine absolute, cassia oil, cinnamon bark oil, rose absolute, orris absolute, lemon essential oil, Bulgarian rose, yara yara, and vanilla; lactones; such as δ-nonalactone, γ-nonalactone, δ-decalactone and δ-dodecalactone, sulfides, e.g., methyl sulfide and other materials such as maltol, acetoin and acetals (e.g., 1,1-diethoxyethane, 1,1-dimethoxyethane and dimethoxymethane).

The specific flavoring adjuvants selected for use may be either solid or liquid depending upon the desired physical form of the ultimate product, i.e., foodstuff, whether simulated or natural, and should, in any event, (i) be organoleptically compatible with the 2,6,6-trimethyl-α-(iso)propenyl-1-cyclohexene-1-methanols and -1,3-cyclohexadiene-1-methanols of our invention by not covering or spoiling the organoleptic properties (aroma and/or taste) thereof; (ii) be non-reactive with the 2,6,6-trimethyl-α-(iso)propenyl-1-cyclohexene-1-methanols and -1,3-cyclohexadiene-1-methanols of our invention and (iii) be capable of providing an environment in which the 2,6,6-trimethyl-α-(iso)propenyl-1-cyclohexene-1-methanols and -1,3-cyclohexadiene-1-methanols of our invention can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of solid products, e.g., simulated foodstuffs, ingredients capable of providing normally solid compositions should be selected.

As will be appreciated by those skilled in the art, the amount of the 2,6,6-trimethyl-α-(iso)propenyl-1-cyclohexene-1-methanols and -1,3-cyclohexadiene-1-methanols employed in a particular instance can vary over a relatively wide range, depending upon the desired organoleptic effects to be achieved. Thus, correspondingly greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected be effective, i.e., sufficient to alter, modify, or enhance the organoleptic characteristics of the parent composition, whether foodstuff per se, chewing gum per se, medicinal product per se, toothpaste per se, or flavoring composition.

The use of insufficient quantities of 2,6,6-trimethyl-α-(iso)propenyl-1-cyclohexene-1-methanols and -1,3-cyclohexadiene-1-methanols will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of 2,6,6-trimethyl-α-(iso)propenyl-1-cyclohexene-1-methanols and -1,3-cyclohexadiene-1-methanols ranging from a small but effective amount, e.g., about 0.05 parts per million up to about 100 parts per million based on total composition are suitable. Concentrations in excess of the maximum quantity stated are not normally recommended, since they fail to provide commensurate enhancement of organoleptic properties. In those instances, wherein 2,6,6-trimethyl-α-(iso)propenyl-1-cyclohexene-1-methanols and -1,3-cyclohexadiene-1-methanols are added to the foodstuff as an integral component of a flavoring composition, it is, of course, essential that the total quantity of flavoring composition employed be sufficient to yield an effective concentration of 2,6,6-trimethyl-α-(iso)propenyl-1-cyclohexene-1-methanols and -1,3-cyclohexadiene-1-methanols in the foodstuff product.

Food flavoring compositions prepared in accordance with the present invention preferably contain 2,6,6-trimethyl-α-(iso)propenyl-1-cyclohexene-1-methanols and -1,3-cyclohexadiene-1-methanols in concentrations ranging from about 0.1% up to about 15% by weight based on the total weight of the said flavoring composition.

The composition described herein can be prepared according to conventional techniques as typified by cake batters and fruit drinks and can be formulated by merely admixing the involved ingredients within the proportions stated in a suitable blender to obtain the desired consistency, homogeneity of dispersion, etc. Alterntively, flavoring compositions in the form of particulate solids can be conveniently prepared by mixing 2,6,6-trimethyl-α-(iso)propenyl-1-cyclohexene-1-methanols and -1,3-cyclohexadiene-1-methanols with, for example, gum arabic, gum tragacanth, carrageenan and the like, and thereafter spray-drying the resultant mixture whereby to obtain the particular solid product. Pre-prepared flavor mixes in powder form, e.g., fruit-flavored powder mix are obtained by mixing the dried solid components, e.g., starch, sugar and the like and 2,6,6-trimethyl-α-(iso)propenyl-1-cyclohexene-1-methanols and -1,3-cyclohexadiene-1-methanols in a dry blender until the requisite degree of uniformity is achieved.

It is presently preferred to combine the 2,6,6-trimethyl-α-(iso)propenyl-1-cyclohexene-1-methanols and -1,3-cyclohexadiene-1-methanols of our invention with the following adjuvants:
p-Hydroxybenzyl acetone;
Geraniol;
Cassia Oil;
Acetaldehyde;
Maltol;
Ethyl methyl phenyl glycidate;
Benzyl acetate;
Dimethyl sulfide;
Eugenol;
Vanillin;
Caryophyllene;
Methyl cinnamate;
Guiacol;
Ethyl pelargonate;
Cinnamaldehyde;
Methyl anthranilate;
5-Methyl furfural;
Isoamyl acetate;
Isobutyl acetate;
Cuminaldehyde;
Alpha ionone;
Cinnamyl formate;
Ethyl butyrate;
Methyl cinnamate;
Acetic acid;
Gamma-undecalactone;
Naphthyl ethyl ether;
Diacetyl;
Furfural;
Ethyl acetate;
Anethole;
2,3-Dimethyl pyrazine;
2-Ethyl-3-methyl pyrazine;
3-Phenyl-4-pentenal;
2-Phenyl-2-hexenal;
2-Phenyl-2-pentenal;
3-Phenyl-4-pentenal diethyl acetal;
β-Damascone (1-crotonyl-2,2,6-trimethylcyclohex-1-ene);
β-Damascenone (1-crotonyl-2,2,6-trimethylcyclohexa-1,3-diene);
α-Damascone;
δ-Damascone;
δ-homocyclocitral (2,2,6-trimethyl-cyclohex-1-ene carboxaldehyde);
Isoamyl butyrate;
Cis-3-hexenol-1;
2-Methyl-2-pentenoic acid;
2-Methyl-cis-3-pentenoic acid;
2-Methyl-cis-3-pentenoic acid ethyl ester;
Elemecine (4-allyl-1,2,6-trimethoxy-benzene);
Isoelemecine (4-propenyl-1,2,6-trimethoxybenzene); and
2-(4-Hydroxy-4-methylpentyl) norbornadiene.

The 2,6,6-trimethyl-α-(iso)propenyl-1-cyclohexene-1-methanols and -1,3-cyclohexadiene-1-methanols of our invention and one or more auxiliary perfume ingredients including for example alcohols other than the 2,6,6-trimethyl-α-(iso)propenyl-1-cyclohexene-1-methanols and -1,3-cyclohexadiene-1-methanols of our invention, aldehydes, nitriles, esters, cyclic esters (lactones), ketones and natural essential oils may be admixed so that the combined odors of the individual components produce a pleasant and desired fragrance, particularly and preferably "honey", "leathery" and "jasmine" fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d)

topnotes which are usually low boiling, fresh-smelling materials.

In perfume compositions, it is the individual components which contribute to their particular olfactory characteristics, however, the overall sensory effect of the perfume composition will be at least the sum total of the effects of each of the ingredients. Thus, one or more of the 2,6,6-trimethyl-α-(iso)propenyl-1-cyclohexene-1-methanol(s) and/or -1,3-cyclohexadiene-1-methanol(s) can be used to alter, modify or enhance the aroma characteristics of a perfume composition, for example, by utilizing or moderating the olfactory reaction contributed by another ingredient in the composition.

The amount of 2,6,6-trimethyl-α-(iso)propenyl-1-cyclohexene-1-methanol(s) and/or -1,3-cyclohexadiene-1-methanol(s) of our invention which will be effective in perfume compositions as well as in perfumed articles and colognes depends on many factors, including the other ingredients, their amounts and the effects which are desired. It has been found that concentrations of as little as 0.01% of the 2,6,6-trimethyl-α-(iso) propenyl-1-cyclohexene-1-methanol(s) and/or -1,3-cyclohexadiene-1-methanol(s) or even less (e.g., 0.005%) can be used to impart leathery, hay, woody, mustard, minty, pulegone-like aroma nuances with hay-tobacco and honey ionone-like topnotes to perfumed articles, e.g., soaps, anionic, cationic or nonionic detergents, cosmetics, fabric softener compositions and/or articles or other products. The amount employed can range up to 70% of the fragrance components and up to 5.0% of the quantity of perfumed article (e.g., soaps, anionic, cationic or nonionic detergent, or fabric softener composition or article) and will depend on considerations of cost, nature of the end product, the effect desired on the finished product and the particular fragrance sought.

The 2,6,6-trimethyl-α-(iso)propenyl-1-cyclohexene-1-methanol(s) and/or -1,3-cyclohexadiene-1-methanol(s) of our invention is (are) useful (taken alone or together with other ingredients in perfume compositions) as (an) olfactory component(s) in detergents and soaps, space odorants and deodorants, perfumes, colognes, toilet water, bath preparations such as lacquers, brilliantines, pomades and shampoos, cosmetic preparations such as creams, deodorants, hand lotions and sun screens; powders such as talcs, dusting powders, face powders and the like. When used as (an) olfactory component(s) as little as 0.1% of 2,6,6-trimethyl-α-(iso)-propenyl-1-cyclohexene-1-methanol(s) and/or -1,3-cyclohexadiene-1-methanol(s) (based on weight of perfume composition) will suffice to impart an intense leather/pulegone/hay-tobacco note to high quality "leather" formulations. Generally, no more than 5% of 2,6,6-trimethyl-α-(iso) propenyl-1-cyclohexene-1-methanol and/or -1,3-cyclohexadiene-1-methanol based on the ultimate end product is required in the perfume composition.

In addition, the perfume composition or fragrance composition of our invention can contain a vehicle or carrier for the 2,6,6-trimethyl-α-(iso)propenyl-1-cyclohexene-1-methanol(s) and/or -1,3-cyclohexadiene-1-methanol(s). The vehicle can be a liquid such as a non-toxic alcohol, a non-toxic glycol, or the like. The carrier can also be an absorbent solid, such as a gum (e.g., gum arabic) or compounds for encapsulating the composition (such as gelatin) for example, by means of coacervation.

An additional aspect of our invention provides an organoleptically improved smoking tobacco product and additives therefor including methods of making the same which overcome problems heretofore encountered in the creation or enhancement of specific desired sweet-musty, hay-tobacco like, fruity-raspberry, ionone-like, fruity-tobacco-like, Virginia tobacco like notes. These notes, both prior to and on smoking in both the main stream and the side stream, may now be readily controlled and maintained at the desired uniform level regardless of variations in the tobacco components of the blend; or the nature of the filter used in conjunction with the smoking tobacco article.

In carrying out this aspect of our invention, we add to smoking tobacco materials or a suitable substitute therefor (e.g., dried lettuce leaves) an aroma and flavor additive containing as an active ingredient, one or more of the 2,6,6-trimethyl-α-(iso) propenyl-1-cyclohexene-1-methanols and/or -1,3-cyclohexadiene-1-methanols of our invention. Other flavoring and aroma additives may be added to the smoking tobacco material or substitute therefor either separately or in admixture with one or more of the 2,6,6-trimethyl-α-(iso)propenyl-1-cyclohexene-1-methanols and -1,3-cyclohexadiene-1-methanols as follows:

I. Synthetic Materials

Beta-methylcinnamaldehyde;
Eugenol;
Dipentene;
β-Damascenone;
Maltol;
Ethyl maltol;
Delta-undecalactone;
Delta-decalactone;
Benzaldehyde;
Amyl acetate;
Ethyl butyrate;
Ethyl valerate;
Ethyl acetate;
2-Hexen-1-ol;
2-Methyl-5-isopropyl-1,3-nonadiene-8-one;
2-Methyl-5-isopropylacetophenone;
2-Hydroxy-2,5,5,8a-tetramethyl-1-(2-hydroxyethyl)-decahydronaphthalene;
Dodecahydro-3a,6,6,9a-tetramethylnaphtho(2,1-b)-furan;
4-Hydroxyhexanoic acid, gamma-lactone;
Polyisoprenoid hydrocarbons filed in Example V of U.S. Pat. No. 3,589,372 issued on June 29, 1971.

II. Natural Oils

Celery seed oil;
Coffee extract;
Bergamot oil;
Cocoa extract;
Nutmeg oil;
Origanum oil.

An aroma and flavoring concentrate containing one or more of the 2,6,6-trimethyl-α-(iso)propenyl-1-cyclohexene-1-methanols and -1,3-cyclohexadiene-1-methanols of our invention and, if desired, one or more of the above-indicated additional flavoring additives may be added to the smoking tobacco material, or to the paper or leaf wrapper or to a filter which is part of the smoking article. The smoking tobacco material may be shredded, cured, cased and blended tobacco material or reconstituted tobacco material or tobacco substitutes (e.g., lettuce leaves) or mixtures thereof. The proportions of flavoring additives may be varied in accordance with taste, but insofar as enhancement or the imparting of sweet-musty, hay-tobacco like, fruity-raspberry, ionone-like, fruity-tobacco like and Virginia tobacco-like notes prior to and on smoking in both the main stream and the side stream, we have found that satisfactory results are obtained if the proportion by weight of the sum total of 2,6,6-trimethyl-α-(iso) propenyl-1-cyclohexene-1-methanols and -1,3-cyclohexadiene-1-methanols to smoking tobacco material is between 50 ppm and 1500 ppm (0.005%–0.15%) of the active ingredients based on the weight of smoking tobacco material. We have further found that satisfactory results are obtained if the proportions by weight of the sum total of 2,6,6-trimethyl-α-(iso)propenyl-1-cyclohexene-1-methanols and -1,3-cyclohexadiene-1-methanols used to flavoring material is between 0.05:1 and 0.50:1.

Any convenient method for incorporating the 2,6,6-trimethyl-α-(iso)propenyl-1-cyclohexene-1-methanols and -1,3-cyclohexadiene-1-methanols in the tobacco product may be employed. Thus, the 2,6,6-trimethyl-α-(iso) propenyl-1-cyclohexene-1-methanols and -1,3-cyclohexadiene-1-methanols taken alone or along with other flavoring ayditives may be dissolved in a suitable solvent such as ethanol, pentane, diethyl ether and/or other volatile organic solvents, and the resulting solution may be either sprayed on the cured, cased and blended tobacco material; or the tobacco material or filter may be dipped into such solution. Under certain circumstances, a solution of 2,6,6-trimethyl-α-(iso)-propenyl-1-cyclohexene-1-methanols and/or -1,3-cyclohexadiene-1-methanols taken alone or taken further together with other flavoring additives as set forth above, may be applied by means of a suitable applicator such as a brush or roller on the paper or leaf wrapper for the smoking product, or it may be applied to the filter by either spraying or dipping or coating.

Furthermore, it will be apparent that only a portion of the tobacco or substitute therefor need be treated, and the thus-treated tobacco may be blended with other tobaccos before the ultimate tobacco product is formed. In such cases, the tobacco treated may have one or more 2,6,6-trimethyl-α-(iso)propenyl-1-cyclohexene-1-methanols and -1,3-cyclohexadiene-1-methanols of our invention in excess of the amounts or concentrations, however, the final product will have the percentage within the indicated range.

In accordance with one specific example of our invention an aged, cured and shredded domestic burley tobacco is sprayed with a 20% ethyl alcohol solution of a 50:50 mixture of cis and trans isomers of 2,6,6-trimethyl-α-propenyl-1,3-cyclohexadiene-1-methanols having the structures:

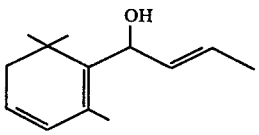

and

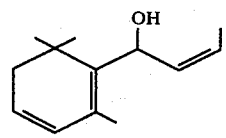

in an amount to provide a tobacco composition containing 600 ppm by weight of 2,6,6-trimethyl-α-propenyl-1,3-cyclohexadiene-1-methanols on a dry basis. Thereafter the alcohol is removed by evaporation, and the tobacco is manufactured into cigarettes by the usual techniques. The cigarettes when treated as indicated have desired and pleasing sweet-musty, hay-tobacco-like, fruity-raspberry, ionone-like aromas prior to smoking and a fruity-tobacco-like, Virginia tobacco-like aroma on smoking in both the main stream and the side streams.

While our invention is particularly useful in the manufacture of smoking tobacco such as cigarette tobacco, cigar tobacco and pipe tobacco, other tobacco products formed from sheeted tobacco dust or fines may also be used. As stated supra, the 2,6,6-trimethyl-α-(iso) propenyl-1-cyclohexene-1-methanols and -1,3-cyclohexadiene-1-methanols of our invention can be incorporated with materials such as filter tip materials, seam paste, packaging materials and the like which are used along with the tobacco to form a product adapted for smoking. Furthermore, the 2,6,6-trimethyl-α-(iso) propenyl-1-cyclohexene-1-methanols and -1,3-cyclohexadiene-1-methanols of our invention can be added to certain tobacco substitutes of natural or synthetic origin (e.g., dried lettuce leaves) and, accordingly, by the term "tobacco" as used throughout this specification is meant any composition intended for human consumption, by smoking or otherwise, whether composed of tobacco plant parts or substitute materials or both.

It will thus be apparent that the 2,6,6-trimethyl-α-(iso)propenyl-1-cyclohexene-1-methanols and -1,3-cyclohexadiene-1-methanols of our invention can be utilized to alter, modify or enhance sensory properties, particularly organoleptic properties, such as flavor(s) and/or fragrance(s) of a wide variety of consumable materials.

The following examples serve to illustrate our invention, and this invention is to be considered restricted thereto only as indicated in the appended claims.

All parts and percentages given herein are by weight unless otherwise specified.

EXAMPLE I

PREPARATION OF 2,6,6-TRIMETHYL-α-ISOPROPENYL-1,3-CYCLOHEXADIENE-1-METHANOL

Reaction:

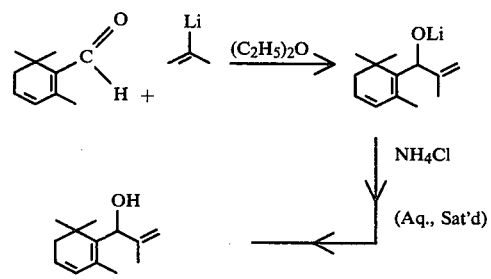

Into a 500 ml reaction flask equipped with immersion thermometer, mechanical stirrer, 250 ml addition funnel, Friedrich's condenser, dry ice/isopropyl alcohol bath and gas bubbler is placed 1.9 grams (44.7 cm length) (0.28 gram atoms) of Li wire (cut up) and 100 ml anhydrous diethyl ether. The lithium wire/diethyl ether mixture is cooled with stirring to −10° C. 15.7 Grams (0.13 moles) of 2-bromo-1-propene (dissolved in approximately 40 ml anhydrous diethyl ether) is added dropwise from the addition funnel into the reaction mixture while maintaining the temperature thereof between −10° C. and −5° C. Following addition of the 2-bromo-1-propene, the reaction mass is stirred for a period of 30 minutes while maintaining the reaction mass at a temperature of 0° C. and is then stirred for 1.5 hours at room temperature (20° C.). The reaction mass is then chilled to −20° C. and 15.0 grams (0.10 moles) of Safranal is added dropwise while maintaining the reaction mass at from −20° up to −15° C. Following the addition of the Safranal, the reaction mass is stirred at −20° C. for a period of 15 minutes and then at room temperature for a period of 2.5 hours. The reaction mass is monitored on GLC at 30 minutes, 90 minutes and 150 minutes, at which point the reaction mass is poured into 300 ml of saturated ammonium chloride (aqueous). The reaction mixture is then added to 200 ml of anhydrous diethyl ether. The reaction mass is then washed with saturated aqueous sodium chloride, dried and concentrated yielding 18.67 grams of crude product. 1.0 Grams of crude product is set aside for silica gel chromatography. The remaining 17.56 grams is vacuum distilled yielding the following fractions:

| Fraction No. | Weight | % Product |
|---|---|---|
| 1 | 0.78 | 84.60% |
| 2 | 4.44 | 91.96% |
| 3 | 2.50 | 94.50% |
| 4 | 1.69 | 95.02% |

Figure 1:
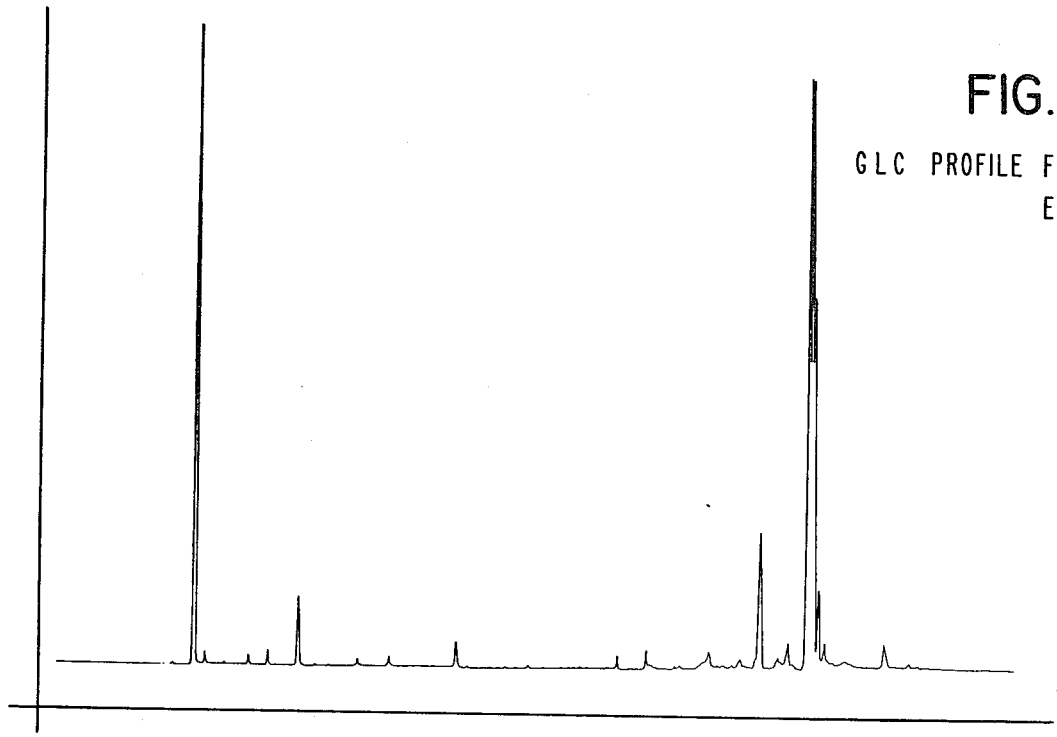
FIG. 1 is the GLC profile for the reaction product of Example I consisting essentially of the compound having the structure.

FIG. 1 is the GLC profile for the product produced according to the above process.

FIG. 2 is the NMR spectrum for the product having the structure:

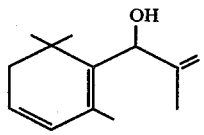

FIG. 3 is the infra-red spectrum for the compound having the structure:

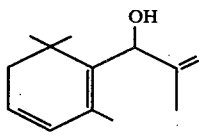

produced according to the above process.

The nuclear magnetic resonance data for the compound having the structure:

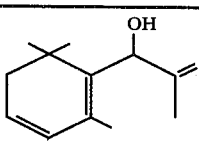

is as follows:

| δ (ppm) | Signal Type | Assignment | Protons |
|---|---|---|---|
| 1.05–1.08 | 2 singlets | H₃C⟋⟍CH₃ | 6 |
| 1.19 | Diffuse | OH | 1 |
| 1.74–1.80 | 2 singlets | (ring-CH₃) + (=CH₃) | 6 |
| 2.01–2.04 | Doublet (J = 2Hz) | H, H (ring) | 2 |
| 4.87 | Broad | OH, H | 1 |
| 4.98 | Apparent doublet AB spectrum | OH, H (vinyl) | 2 |
| 5.68 | Singlet | OH, ring H, H | 2 |

The mass spectral analysis for the compound having the structure is as follows:

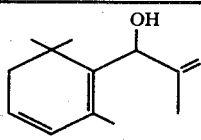

| M/E | Relative Intensity |
|---|---|
| 41 | 30 |
| 43 | 24 |
| 71 | 55 |
| 91 | 38 |
| 105 | 33 |
| 107 | 47 |
| 121 | 65 |
| 159 | 100 |
| 174 | 38 |
| 192p | 23 |

EXAMPLE II

Honey Formulation

The following mixture is prepared:

| Ingredients | Parts by Weight |
|---|---|
| Phenylacetic acid | 70.0 |
| Coumarin | 20.0 |
| Phenylethylphenyl acetate | 100.0 |
| Phenyl ethyl alcohol | 5.0 |
| Benzyl benzoate | 100.0 |
| Dimethylphenylethyl carbinol | 10.0 |
| Methyl anthranilate | 5.0 |
| Beta ionone | 10.0 |
| 2,4,4,6-tetramethyl-2,5- | 30.0 |

-continued

| Ingredients | Parts by Weight |
|---|---|
| cyclohexadien-1-one | |
| 2,6,6-trimethyl-α-isopropenyl-1,3-cyclohexadiene-1-methanol produced according to Example I | 2.0 |

The 2,4,4,6-tetramethyl-2,5-cyclohexadien-1-one imparts a warm, sweet, slightly minty, woody note to this honey formulation. However, the 2,6,6-trimethyl-α-isopropenyl-1,3-cyclohexadiene-1-methanol produced according to Example I adds a leathery, spicey (clove), minty note to the formulation and enhances the leathery character thereof.

EXAMPLE III

The following mixture is prepared:

| Ingredients | Parts by Weight |
|---|---|
| Para-cresol | 3.0 |
| Methyl N-acetylanthranilate | 20.0 |
| Farnesol | 3.0 |
| Nerolidol | 20.0 |
| Cis-3-hexenyl benzoate | 30.0 |
| Indol | 15.0 |
| Eugenol | 35.0 |
| Benzyl alcohol | 50.0 |
| Methyl linoleate | 100.0 |
| Jasmine lactone | 30.0 |
| Dihydro methyl jasmonate | 20.0 |
| Benzyl acetate | 500.0 |
| Cis-jasmone | 40.0 |
| Linalool | 200.0 |
| 4-butyl-3,4,5-trimethyl-2,5-cyclohexadien-1-one (prepared according to the process of Example V of U.S. Letters Pat., Serial No. 860,121 filed December 13, 1977 | 50.0 |
| 2,6,6-trimethyl-α-isopropenyl-1,3-cyclohexadiene-1-methanol produced according to Example I | 15.0 |

The 4-butyl-3,4,5-trimethyl-2,5-cyclohexadien-1-one imparts a green, herbaceous, floralcy of Jasmine to this Jasmine formulation. The 2,6,6-trimethyl-α-isopropenyl-1,3-cyclohexadiene-1-methanol produced according to Example I imparts a leather note with a spicey, minty topnote to this Jasmine formulation thereby enhancing it.

EXAMPLE IV

Preparation of a Cosmetic Powder Composition

A cosmetic powder is prepared by mixing in a ball mill, 100 g of talcum powder with 0.25 g of 2,6,6-trimethyl-α-isopropenyl-1,3-cyclohexadiene-1-methanol produced according to Example I. It has an excellent leathery, minty, pulegone-like aroma with hay, tobacco, spicey (clove-like) topnotes.

EXAMPLE V

Utilizing the procedure of Example I of column 15 of U.S. Pat. No. 3,632,396, a nonwoven cloth substrate useful as a dryer-added fabric-softening article of manufacture is prepared wherein the substrate, the substrate coating and the outer coating and the perfuming material are as follows:
1. a water "dissolvable" paper ("Dissolvo Paper");
2. Adogen 448 (m.p. about 140° F.) as the substrate coating; and
3. an outer coating having the following formulation (m.p. about 150° F.):
   - 57 percent $C_{20-22}$ HAPS
   - 22 percent isopropyl alcohol
   - 20 percent antistatic agent
   - 1 percent of 2,6,6-trimethyl-α-isopropenyl-1,3-cyclohexadiene-1-methanol produced according to Example I giving rise to a leathery, minty, pulegone-like aroma with hay-tobacco and spicey (clove-like) topnote.

A fabric-softening composition prepared as set forth above having the above aroma characteristics essentially consists of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and outer coating weight ratio of about 1:1 by weight of the substrate. The aroma as set forth above is imparted in a pleasant manner to the head space in the dryer on operation thereof using the said dryer-added fabric-softening nonwoven fabric.

EXAMPLE VI

Perfumed Liquid Detergent

Concentrated liquid detergents (Lysine salt of n-dodecylbenzene sulfonic acid as more specifically described in U.S. Pat. No. 3,948,818, issued on Apr. 6, 1976) with a leathery, minty, pulegone-like aroma and hay-tobacco topnotes are prepared containing 0.10%, 0.15%, 0.20%, 0.25% and 0.30% of 2,6,6-trimethyl-α-isopropenyl-1,3-cyclohexadiene-1-methanol prepared according to Example I. They are prepared by adding and homogeneously mixing the appropriate quantity of 2,6,6-trimethyl-α-isopropenyl-1,3-cyclohexadiene-1-methanol in the liquid detergent. The detergents all possess leathery, minty, pulegone-like aromas with hay-tobacco and spicey (clove-like) topnotes.

EXAMPLE VII

Preparation of a Cologne and Handkerchief Perfume 2,6,6-Trimethyl-α-isopropenyl-1,3-cyclohexadiene-1-methanol prepared according to Example I is incorporated into colognes at concentrations of 2.0%, 2.5%, 3.0%, 3.5%, 4.0%, 4.5% and 5.0% in 85% aqueous food grade ethyl alcohol; and into handkerchief perfumes at concentrations of 15%, 20%, 25%, 30% and 35% (in 95% aqueous food grade ethanol). Distinct and definite leathery, minty, pulegone-like aromas with hay-tobacco and spicey (clove-like) topnotes are imparted to the cologne and to the handkerchief perfumes.

EXAMPLE VIII

Preparation of Soap Composition

One hundred grams of soap chips are mixed with one gram of 2,6,6-trimethyl-α-isopropenyl-1,3-cyclohexadiene-1-methanol produced according to Example I until a homogeneous composition is obtained. The perfumed soap composition manifests a leathery, minty, pulegone-like aroma with hay-tobacco and spicey (clove-like) topnotes.

EXAMPLE IX

Preparation of a Detergent Composition

A total of 100 g of a detergent powder (Lysine salt of n-dodecylbenzene sulfonic acid as more specifically described in U.S. Pat. No. 3,948,818, issued on Apr. 6, 1976) is mixed with 0.15 g of the 2,6,6-trimethyl-α-isopropenyl-1,3-cyclohexadiene-1-methanol of Example I until a substantially homogeneous composition is obtained. This composition has an excellent leathery, minty, pulegone-like aroma with hay-tobacco and spicey (clove-like) topnotes.

EXAMPLE X

A tobacco blend is made by mixing the following materials.

| Ingredient | Parts by Weight |
|---|---|
| Bright | 40.1 |
| Burley | 24.9 |
| Maryland | 1.1 |
| Turkish | 11.6 |
| Stem (flue cured) | 14.2 |
| Glycerine | 2.8 |
| Water | 5.3 |

The above tobacco is used in producing cigarettes, and the following is compounded and incorporated into each of these cigarettes:

| Ingredient | Parts by Weight |
|---|---|
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above flavor is incorporated into model "filter" cigarettes at the rate of 0.1%. One-third of these model cigarettes are treated in the tobacco section with 2,6,6-trimethyl-α-isopropenyl-1,3-cyclohexadiene-1-methanol produced according to Example I at 100 ppm per cigarette. Another one-third of these model cigarettes are treated in the filter with the 2,6,6-trimethyl-α-isopropenyl-1,3-cyclohexadiene-1-methanol produced according to Example I at the rate of $2 \times 10^{-5}$ gm and $3 \times 10^{-5}$ gm. When evaluated by paired comparison, the cigarettes treated both in the tobacco and in the filter with the 2,6,6-trimethyl-α-isopropenyl-1,3-cyclohexadiene-1-methanol are found, in smoke flavor, to be more tobacco-like with enhanced Virginia tobacco-like notes.

EXAMPLE XI

Preparation of 2,6,6-trimethyl-α-n-propenyl-1,3-cyclohexadiene-1-methanol

Reaction:

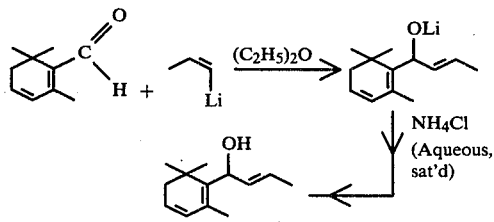

Into a 500 ml reaction flask equipped with immersion thermometer, mechanical stirrer, 250 ml addition funnel, Freidrich's condenser, dry-ice/isopropyl alcohol bath and gas bubbler is placed 1.9 grams (0.28 gram atoms) of lithium wire cut up (44.7 cm in length), and 100 ml anhydrous diethyl ether. The lithium/diethyl ether mixture is cooled with stirred to −10° C. 15.7 Grams (0.13 moles) of 1-bromo-1-propene dissolved in 40 ml diethyl ether is then added dropwise from the addition funnel while maintaining the reaction temperature at from −10° up to −5° C. Following addition of the 1-bromo-1-propene, the reaction mass is stirred for 30 minutes at 0° C. and for a period of 1.5 hours at 20° C. The reaction mass is then chilled to −20° C. and 15.0 grams of Safranal (0.10 moles) in approximately 60 ml diethyl ether is added to the reaction mass dropwise while maintaining the temperature between −20° and −15° C. Following additional of the sanfranal, the reaction mass is stirred at about −20° C. for a period of 15 minutes and at room temperature (20° C.) for a period of 2.5 hours. The reaction mass is monitored using GLC at 30 minutes, 90 minutes and 150 minutes, at which point, the reaction mass is poured into saturated aqueous ammonium chloride. The resulting mixture is then washed with diethyl ether and the aqueous phase is separated from the organic phase. The organic phase is dried and concentrated in 18.67 grams of oil. 1.0 Grams of crude is set aside for silica gel chromatography; 0.1 grams is set aside for GLC; and the remaining 17.56 grams is distilled in a vacuum distillation apparatus after adding 0.9 grams of sodium carbonate and 19.0 grams of Primol ® yielding the following fractions:

| Fraction No. | Vapor Temp. | Liquid Temp. | Vacuum (mm Hg) | Weight of Product |
|---|---|---|---|---|
| 1 | 24/102 | 25/117 | 0.6 | 0.52 |
| 2 | 94 | 116 | 0.5 | 1.96 |
| 3 | 96 | 118 | 0.6 | 2.14 |
| 4 | 93 | 128 | 0.6 | 3.01 |
| 5 | 85.5 | 153 | | 1.66 |

The total yield is 9.29 grams which is equivalent to 48.38%.

The GLC profile for the reaction product is set forth in FIG. 4.

The NMR spectrum for the resulting mixture of fractions 1–4 is ascertained to be a 70:30 trans:cis isomer mixture of compounds having the following structures:

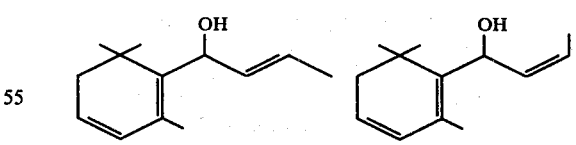

FIG. 6 is the infra-red spectrum for the 70:30 trans:cis isomer mixture of the compounds having the structures:

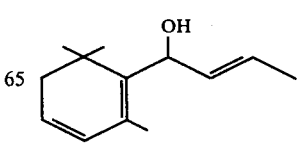

and

-continued

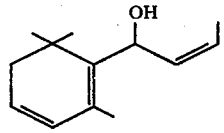

FIG. 7 is the NMR spectrum for the cis isomer having the structure:

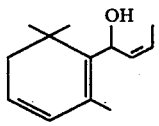

FIG. 8 is the NMR spectrum for the trans isomer having the structure:

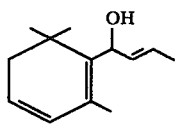

FIG. 9 is the infra-red spectrum of the trans isomer having the structure:

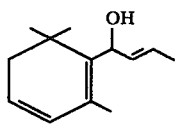

The NMR analysis for the trans isomer having the structure:

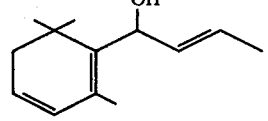

is as follows:

| δ (ppm) | Signal Type | Assignment | Protons |
|---|---|---|---|
| 1.05–1.12 | 2 Singlets | H₃C, CH₃ | 6 |
| 1.72 | Doublet | OH, CH₃ | 3 |
| 1.88 | Singlet | CH₃ | 3 |
| 2.01 | Doublet | H, H | 2 |
| 5.32 | Doublet | OH, H | 1 |
| 5.66 | Multiplet | + H, H | 4 |

-continued

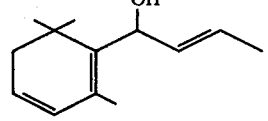

is as follows:

| δ (ppm) | Signal Type | Assignment | Protons |
|---|---|---|---|

OH H / H

The NMR analysis for the cis isomer having the structure:

is as follows:

| δ (ppm) | Signal Type | Assignment | Protons |
|---|---|---|---|
| 1.04–1.10 | 2 Singlets | H₃C, CH₃ | 6 |
| 1.73 | Doublet | OH CH₃ | 3 |
| 1.82 | Singlet | CH₃ | 3 |
| 1.88 | Singlet | —OH | 1 |
| 2.02 | Doublet | H, H | 2 |
| 4.98 | Broad | OH, H | 1 |
| 5.66 | Broad Singlet | + | 4 |

The mass spectrum for the cis isomer is as follows:

| M/E | Relative Intensity |
|---|---|
| 39 | 28 |
| 41 | 40 |
| 43 | 30 |
| 69 | 61 |
| 71 | 74 |
| 91 | 51 |
| 105 | 52 |
| 107 | 26 |
| 119 | 80 |
| 121 | 70 |
| 159 | 100 |
| 174 | 28 |
| 179 | 11 |

-continued

| M/E | Relative Intensity |
|---|---|
| 192p | 41 |

The mass spectral analysis for the trans isomer is as follows:

| M/E | Relative Intensity |
|---|---|
| 39 | 23 |
| 41 | 47 |
| 43 | 32 |
| 69 | 95 |
| 71 | 100 |
| 91 | 29 |
| 105 | 32 |
| 107 | 21 |
| 119 | 22 |
| 121 | 54 |
| 159 | 33 |
| 174 | 10 |
| 177 | 3 |
| 192p | 14 |

EXAMPLE XII

Preparation of 2,6,6-trimethyl-α-n-propenyl-1,3-cyclohexadiene-1-methanol

Reaction:

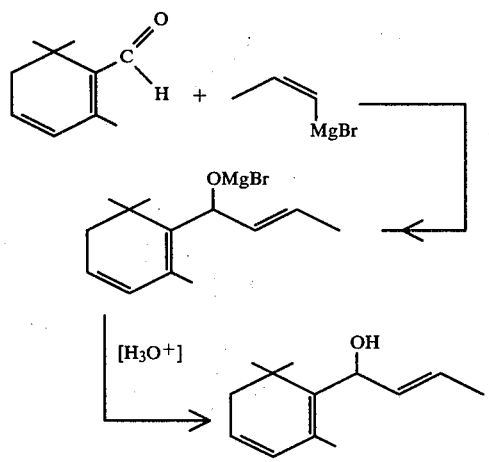

Into a one liter reaction flask under nitrogen atmosphere equipped with stirrer, thermometer and reflux condenser is charged 24 g of magnesium ribbon (1.0 moles) and 200 ml tetrahydrofuran. A mixture of 150 ml tetrahydrofuran and 100 g of 1-bromo-1-propene (0.83 moles) is then slowly added to the reaction mass while maintaining the reaction mass at 25°–30° C. using a cooling bath. When the addition is complete, 100 g of safranal (0.67 moles) dissolved in 100 ml tetrahydrofuran is added over a three-hour period while maintaining the reaction mass at a temperature of between 20° C. and 35° C.

The reaction mass is then filtered and stripped of solvent yielding 100 g of crude product. 2.0 Grams of triethanolamine is then added to the reaction mass which is distilled on a microvigreux column yielding the following fractions:

| Fraction # | Vapor Temp. | Liquid Temp. | Vac. mm/Hg |
|---|---|---|---|
| 1 | 85/87 | 104/105 | 3.6/3.6 |
| 2 | 85 | 103 | 2.4 |
| 3 | 82 | 104 | 1.6 |
| 4 | 81 | 104 | 1.6 |
| 5 | 97 | 126 | 1.3 |
| 6 | 102 | 141 | 1.2 |
| 7 | 107 | 147 | 1.8 |
| 8 | 91/132 | 142/180 | 0.8/0.8 |
| 9 | 145 | 190 | 0.8 |

The resulting product is odor evaluated and fractions 4–8 are bulked. Fractions 4–8 contain primarily 2,6,6-trimethyl-α-propenyl-1,3-cyclohexadiene-1-methanol having one of the structures or both of the structures:

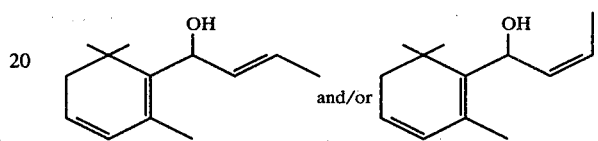

as confirmed by NMR, IR and Mass Spectral analyses.

The reaction product has a very strong, hay, safranal-like, woody, mustard note with honey ionone-like topnotes.

EXAMPLE XIII

Preparation of a Detergent Composition

A total of 100 g of a detergent powder (Lysine salt of n-dodecylbenzene sulfonic acid as more specifically described in U.S. Pat. No. 3,948,818 issued on Apr. 6, 1976) is mixed with 0.15 g of 2,6,6-trimethyl-α-propenyl-1,3-cyclohexadiene-1-methanol produced according to Examples XI or XII until a substantially homogeneous composition is obtained. This composition has a very strong hay, safranal-like, woody mustard aroma with honey/ionone topnotes.

EXAMPLE XIV

Perfumed Liquid Detergent

Concentrated liquid detergents (Lysine salt of n-dodecylbenzene sulfonic acid as more specifically described in U.S. Pat. No. 3,948,818 issued on Apr. 6, 1976) with a very strong hay, safranal-like, woody, mustard aroma with honey ionone topnotes are prepared containing 0.10%, 0.15%, 0.20%, 0.25% and 0.30% of 2,6,6-trimethyl-α-propenyl-1,3-cyclohexadiene-1-methanol prepared according to Examples XI or XII. They are prepared by adding and homogeneously mixing the appropriate quantity of 2,6,6-trimethyl-α-propenyl-1,3-cyclohexadiene-1-methanol in the liquid detergent. The detergents all possess very strong hay, safranal-like, woody, mustard aromas with honey/ionone topnotes.

EXAMPLE XV

Preparation of a Cologne and Handkerchief Perfume 2,6,6-Trimethyl-α-propenyl-1,3-cyclohexadiene-1-methanol prepared according to Examples XI or XII is incorporated into colognes at concentrations of 2.0%, 2.5%, 3.0%, 3.5%, 4.0%, 4.5% and 5.0% in 85% aqueous food grade ethyl alcohol; and into handkerchief perfumes at concentrations of 15%, 20%, 25%, 30% and 35% (in 95% aqueous food grade ethanol). Distinct and definite very strong hay, safranal-like, woody, mustard aromas with honey/ionone topnotes are imparted to the colognes and to the handkerchief perfumes.

EXAMPLE XVI

Utilizing the procedure of Example I of column 15 of U.S. Pat. No. 3,632,396, a nonwoven cloth substrate useful as a dryer-added fabric-softening article of manufacture is prepared wherein the substrate, the substrate coating and the outer coating and the perfuming material are as follows:

1. a water "dissolvable" paper ("Dissolvo Paper");
2. Adogen 448 (m.p. about 140° F.) as the substrate coating; and
3. an outer coating having the following formulation (m.p. about 150° F.);
    57 percent $C_{20-22}HAPS$
    22 percent isopropyl alcohol
    20 percent antistatic agent
    1 percent of 2,6,6-trimethyl-α-n-propenyl-1,3-cyclohexadiene-1-methanol produced according to Examples XI or XII giving rise to a very strong hay, safranal-like, woody, mustard aroma with honey/ionone topnotes.

A fabric-softening composition prepared as set forth above having the above aroma characteristics essentially consists of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and outer coating weight ratio of about 1:1 by weight of the substrate. The aroma as set forth above is imparted in a pleasant manner to the head space in the dryer on operation thereof using the said dryer-added fabric-softening nonwoven fabric.

EXAMPLE XVII

Preparation of
2,6,6-trimethyl-α-isopropenyl-1-cyclohexene-1-methanol

Reaction:

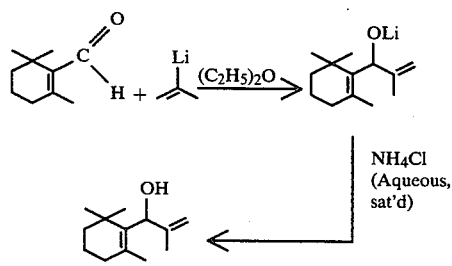

Into a 500 ml flask equipped with immersion thermometer, mechanical stirrer, 250 ml addition funnel, Friedrich's condenser, dry-ice/isopropyl alcohol bath and gas bubbler is placed 1.9 grams (44.7 cm in length) (0.28 gram atoms) of cut up lithium wire and 100 ml anhydrous diethyl ether. The lithium/diethyl ether mixture is cooled to −10° C. 15.7 Grams (0.13 moles) of 2-bromo-1-propene (dissolved in approximately 40 ml anhydrous diethyl ether) is added drop-wise to the reaction mass keeping the temperature at between −10° C. and −5° C. Following addition of the 2-bromo-1-propene, the reaction mass is stirred for a period of 30 minutes at 0° C. and for a period of 1.5 hours at room temperature (20° C.). The reaction mass is then chilled to −20° C. and 15.2 grams (0.10 moles) of beta cyclocitral (dissolved in approximately 60 ml diethyl ether) is added dropwise while keeping the reaction temperature at between −20° C. and −15° C. After addition of the beta cyclocitral, the reaction mass is stirred for a period of 15 minutes at −20° C.; and for a period of 120 minutes at +24° C. The reaction mass is then poured into a saturated aqueous ammonium chloride solution, and the resulting organic phase is separated from the aqueous phase. The aqueous phase is washed with anhydrous diethyl ether. The organic phase is washed with saturated brine. The organic phase and the ether extracts are combined and the resulting material is dried and concentrated in yield 19.98 grams of crude material. This material is distilled under vacuum to 5 fractions as follows:

| Fraction No. | Weight | % Product |
|---|---|---|
| 1 | 4.94 | 79.40% |
| 2 | 3.24 | 94.37% |
| 3 | 3.64 | 95.44% |
| 4 | 1.73 | 96.15% |
| 5 | 1.32 | 96.10% |

The fractional distillation data is as follows:

| Fraction No. | Vapor Temp. | Liquid Temp. | Vacuum (mm Hg) | Weight of Fraction |
|---|---|---|---|---|
| 1 | 23/72 | 26/87.5 | 0.25 | 4.94 |
| 2 | 79.5 | 89 | 0.25 | 3.24 |
| 3 | 69 | 95 | 0.25 | 3.64 |
| 4 | 64.5 | 112 | 0.25 | 1.73 |
| 5 | 60.0 | 152 | 0.25 | 1.32 |

The resulting reaction product has the structure:

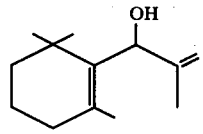

as confirmed by NMR, IR and mass spectral analyses.

The GLC profile for the reaction product is set forth in FIG. 10.

The NMR spectrum for the compound having the structure:

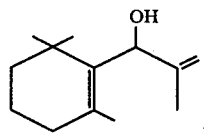

is set forth in FIG. 11.

The infrared spectrum for the compound having the structure:

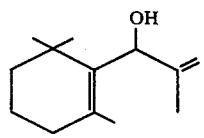

is set forth in FIG. 12.

The NMR analysis is as follows:

| δ (ppm) | Signal Type | Assignment | Protons |
|---|---|---|---|
| 0.99–1.13 | 2 Singlets | H₃C⎯CH₃ | 6 |
| 1.39–1.68 | Multiplet | (structure with 4 H) | 4 |
| 1.65–1.73 | 2 Singlets | OH, CH₃, CH₃ | 6 |
| 1.88–2.00 | Diffuse Triplet | (structure with H H) | 2 |
| 4.68 | Apparent Doublet AB Spectrum | OH H | 2 |
| 4.97 | Broad | OH | 1 |

The mass spectral analysis for the compound having the structure:

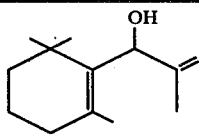

is as follows:

| M/E | Relative Intensity |
|---|---|
| 41 | 54 |
| 55 | 30 |
| 91 | 42 |
| 105 | 90 |
| 107 | 46 |
| 119 | 56 |
| 120 | 52 |
| 133 | 35 |
| 161 | 100 |
| 176 | 68 |
| 179 | 24 |
| 194p | 7 |

EXAMPLE XVIII

Otto of Rose Perfume Formulation

The following mixture is prepared:

| Ingredients | Parts by Weight |
|---|---|
| Phenyl acetic acid | 5 |
| Hydroxycitronellal | 10 |
| Geraniol | 125 |
| Citronellol | 150 |
| Phenyl ethyl alcohol | 50 |
| Phenyl ethyl acetate | 4 |
| Ethyl phenyl acetate | 5 |
| Citronellyl formate | 20 |
| Geranyl acetate | 25 |
| Linalool | 15 |
| Terpineol | 10 |
| Eugenol | 3 |

-continued

| Ingredients | Parts by Weight |
|---|---|
| Phenyl acetaldehyde dimethyl acetal | 5 |
| Benzyl acetate | 3 |
| Guaiacwood oil | 5 |
| 3-Methylthio-4-heptanone produced according to the process of Part "C" of Example I of U.S. Pat. No. 4,065,408 issued on December 27, 1977 | 5 |
| Bulked fractions 1–4 of the reaction product of Example XVII having the structure: 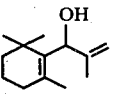 | 5 |

The use of the 3-methylthio-4-heptanone herein imparts a green, fruity, spicey topnote to this Otto of Rose perfume formulation. The combination of the 3-methylthio-4-heptanone together with the product produced according to Example XVII (bulked fractions 1–4, inclusive) causes the Otto of Rose perfume formulation to be much more "natural-like" with floral, woody, oriental and heavy fruity undertones.

EXAMPLE XIX

Preparation of a Soap Composition

Chips of soap comprising 17% coconut fatty acid soap and 83% hydrogenated tallow acids sodium soap are mixed with titanium dioxide (a white pigment), preservative, the perfume composition of Example XVIII, a bacteriostat and miscellaneous additives in the proportions given below:

| Ingredient | Percent |
|---|---|
| 17:83 coco:tallow sodium soap chips | 95.85 |
| Titanium dioxide | 0.50 |
| Preservative | 0.15 |
| Perfume composition prepared according to Example XVIII | 1.50 |
| Bacteriostat | 1.00 |
| Miscellaneous Additives | 1.00 |

The soap chips, white pigment, preservative, perfume composition prepared according to Example XVIII, bacteriostat and additives are mixed and milled. The milled chips are fed into the top worm of a 4" double-barrel vacuum plodder.

After the segments pass through the die plate as described in the drawings of United Kingdom Patent 1,494,278, a 10% aqueous dispersion of a blue pigment (Monastral ® Green GWD available from E. I. duPont de Nemours, U.S.A.—"Monastral" is a trademark) is sprayed onto the segments at a predetermined rate of about half a pound of pigment dispersion per 100 pounds of soap.

The die plate used has circular holes each having a diameter of 1.25 inches and is more particularly described in Example I of United Kingdom Pat. No. 1,494,278. The knife has four blades and is rotated at a sufficient speed to produce segments 2 inches long. The geometric ratio is 5. The final soap bar has a distinct marbled appearances with an undiluted white background, bright blue colored areas and a clear demarcation between the white and blue areas. The resulting soap also has an excellent Otto of Rose type aroma with distinct floral, woody, oriental and heavy fruity undertones and hay and slightly camphoraceous topnotes.

EXAMPLE XX

Preparation of a Soap Composition

100 Grams of soap chips prepared according to Example XIX but without any perfume added is then mixed with 1 gram of the bulked fractions 1-4 of the distillation product of the reaction mass produced according to Example XVII until a substantially homogeneous composition is obtained. The perfumed mixture is then heated to a temperature of 150° C. and maintained at that temperature for a period of 20 minutes. The mixture is then molded into a soap bar and permitted to cool to room temperature. The resulting soap bar has an excellent floral, rose-like aroma with heavy fruity (berry) nuances and woody and oriental topnotes.

EXAMPLE XXI

Preparation of a Detergent Composition

A total of 100 grams of a detergent powder (a nonionic detergent powder containing a proteolytic enzyme prepared according to Example I of Canadian Pat. No. 985,190 issued on Mar. 9, 1976) is mixed with 0.10, 0.15, 0.20, 0.25 or 0.30 grams of the distillation product of the reaction mass prepared according to Example XVII (bulked fractions 1-4) until a substantially homogeneous composition is obtained. The composition has an excellent floral, rose-like aroma with a heavy fruity (berry) undertone and woody and oriental topnotes.

EXAMPLE XXII

A total of 100 grams of a detergent powder (a nonionic detergent powder containing a proteolytic enzyme prepared according to Example I of Canadian Pat. No. 985,190 issued on Mar. 9, 1976) is mixed with 0.10, 0.15, 0.20, 0.25 or 0.30 grams of the perfume composition prepared according to Example XVIII until a substantially homogeneous composition is obtained. This composition has an excellent Otto of Rose aroma with floral, heavy fruity nuances and woody and oriental topnotes.

EXAMPLE XXIII

Perfumed Liquid Detergents

Concentrated liquid detergents with rich, pleasant Otto of Rose aromas are prepared containing 0.10%. 0.15%, 0.20%, 0.25% or 0.30% of the compound prepared according to Example XVII. They are prepared by adding and homogeneously admixing the appropriate quantity of the compound of Example XVII in the liquid detergent. The liquid detergents are all produced using anionic detergents containing a 50:50 mixture of sodium lauroyl sarcosinate and potassium N-methyl lauroyl tauride. The detergents all possess a pleasant Otto of Rose fragrance with floral and heavy fruity undertones and woody and oriental set of topnotes.

EXAMPLE XXIV

Handkerchief Perfume and Cologne Preparation

The perfume composition described in Example XVIII is incorporated in colognes at concentrations of 2.0%, 2.5%, 3.0%, 4.0% and 5.0% in 85% aqueous food grade ethanol and into handkerchief perfumes at concentrations of 15%, 20%, 25%, 30%, and 40% (in 95% aqueous food grade ethanol). Distinctive and definitive strong Otto of Rose fragrances with floral, rose-like and heavy fruity nuances and woody and oriental topnotes are produced in the colognes and handkerchief perfumes.

EXAMPLE XXV

Perfumed Shampoo

The hair cosmetic agents shown in Table I are incorporated into a base shampoo having the following composition:

| Ingredients | Percent by Weight |
|---|---|
| Ammonium lauryl sulphate | 18.0 |
| Lauric isopropanolamide | 1.0 |
| Texicryl 13-300 ® | about 1.0 |
| Hair cosmetic agent of Table I | 1.0 to 12.0 |
| Color | 0.5 |
| Perfume | 0.5 |
| Water | Balance to 100.0 |

Texicryl 13-300 is a registered trademark and is a brand of an aqueous emulsion of a carboxylated acrylic copolymer available from Scott Bader & Co. Ltd.

The amount of Texicryl 13-300 in the shampoo is adjusted according to the nature of the hair cosmetic agent used so that the viscosity of the shampoo is from 500 to 2,500 cps.

The pH of the shampoo is adjusted to 6.5 or greater.

TABLE I

| Example No. | Hair Cosmetic Agent | % by weight in base shampoo |
|---|---|---|
| XXV(a) | Ethoxylated lanolin and Glycerol monostearate in 50:50 ratio | 2.0 |
| XXV(b) | Long chain fatty condensate | 5.0 |
|  | Glycerol monostearate | 2.0 |
|  | ("Alcamine" resin supplied by Allied Colloids Ltd., Low Moor, Bradford, Yorkshire, England) | 0.5 |
| XXV(c) | Olive oil | 1.0 |
| XXV(d) | Olive oil | 2.0 |
| XXV(e) | (Lanolin alcohol and | 3.0 |
|  | Ethylene glycol monostearate) | 1.0 |
| XXV(f) | (Lanolin alcohol and | 4.0 |
|  | Ethylene glycol monostearate) | 1.0 |

A second series of compositions is formulated by incorporating the hair cosmetic agents shown in Table I into the above base shampoo.

In an amount of 1% (1 part by weight per 100 parts by weight of the shampoo) the compound having the structure:

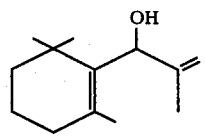

(bulked fractions 1-4) produced according to Example XVII is added to the shampoo of each of Example XXV (a), (b), (c), (d), (e) and (f). In each of the shampoos, an excellent floral, rose-like aroma with a heavy fruity (berry) undertone and woody and oriental topnotes is imparted.

EXAMPLE XXVI

Raspberry Flavor Formulation

The following basic raspberry flavor formulation is produced.

| Ingredient | Parts by Weight |
| --- | --- |
| Vanillin | 2.0 |
| Maltol | 5.0 |
| Parahydroxybenzylacetone | 5.0 |
| Alpha-ionone (10% in Propylene glycol) | 2.0 |
| Ethyl butyrate | 6.0 |
| Ethyl acetate | 16.0 |
| Dimethyl sulfide | 1.0 |
| Isobutyl acetate | 13.0 |
| Acetic acid | 10.0 |
| Acetaldehyde | 10.0 |
| Propylene glycol | 930.0 |
| TOTAL | 1000.0 |

The mixture of compounds having the structures:

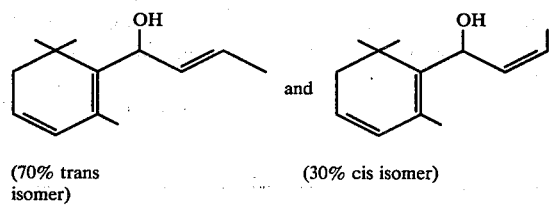

(70% trans isomer)    (30% cis isomer)

prepared according to Example XI is added to half of the above formulation at the rate of 0.02%. The formulation with the mixture of compounds prepared according to Example XI is compared with the formulation without the mixture of such compounds at the rate of 0.01% (100 ppm) in water and evaluated by a bench panel.

The flavor containing the mixture of compounds having the structures:

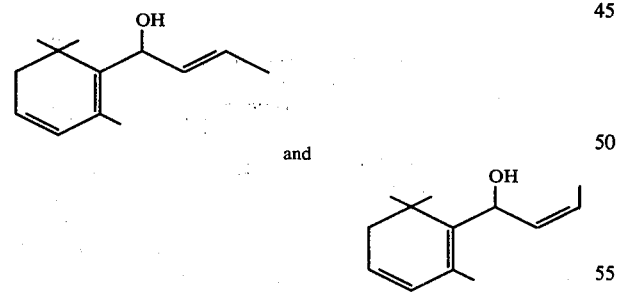

is found to have a substantially more pleasant and better raspberry aroma and taste. It is the unanimous opinion of the bench panel that the chemicals which are the compounds in admixture having the structures:

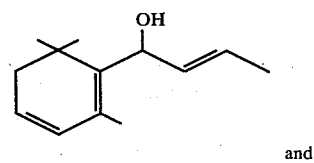

and

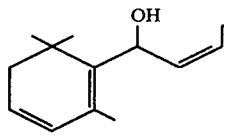

round the flavor out and contribute to a very natural fresh aroma and taste as found in full, ripe raspberries. Accordingly, the addition of the compounds having the structures:

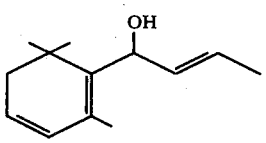

and

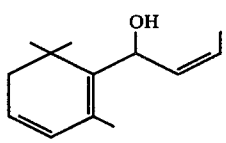

as described above is considered to create a substantially better flavor than the flavor without said compounds.

EXAMPLE XXVII

Tobacco Formulation

A tobacco mixture is produced by admixing the following ingredients:

| Ingredients | Parts by Weight |
| --- | --- |
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco.

The following flavor formulation is prepared:

| Ingredients | Parts by Weight |
| --- | --- |
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above-stated tobacco flavor formulation is applied at the rate of 1.0% to all of the cigarettes produced using the above tobacco formulation. Half of the cigarettes are then treated with 150 or 250 ppm of the mixture of cis and trans isomers (70:30 trans:cis isomer ratio) produced according to Example XI having the structures:

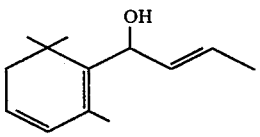

and

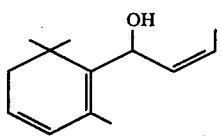

The control cigarettes not containing the mixture of cis and trans isomers produced according to the process of Example XI and the experimental cigarettes which contain the mixture of the cis and trans isomers produced according to Example XI are evaluated by paired comparison and the results are as follows:

The experimental cigarettes are found to have more body in tobacco smoke flavor and a fuller body sensation. The tobacco-like notes are enhanced and the flavor of the tobacco on smoking is more aromatic with floral, sweety, fruity, hay, minty/spicey and woody aroma and taste nuances.

The tobacco smoke flavor of the experimental cigarettes has sweet, fruity, hay, musty, minty/spicey, and woody notes. All cigarettes are evaluated for smoke flavor with a 20 mm cellulose acetate filter.

When the mixture of compounds having the structure:

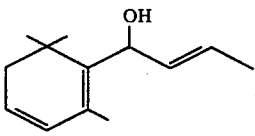

and

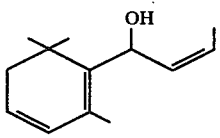

is added to the filter rather than to the tobacco at either 50 ppm or 100 ppm, an interesting and pleasant sweet, fruity aroma is obtained prior to and on smoking the cigarettes.

EXAMPLE XXVIII

Raspberry Flavor Formulation

The following basic raspberry flavor formulation is produced:

| Ingredient | Parts by Weight |
|---|---|
| Vanillin | 2.0 |
| Maltol | 5.0 |
| Parahydroxybenzylacetone | 5.0 |
| Alpha-ionone (10% in Propylene glycol) | 2.0 |
| Ethyl butyrate | 6.0 |
| Ethyl acetate | 16.0 |
| Dimethyl sulfide | 1.0 |
| Isobutyl acetate | 13.0 |
| Acetic acid | 10.0 |
| Acetaldehyde | 10.0 |
| Propylene glycol | 930.0 |
| TOTAL | 1000.0 |

α-Isopropenyl-2,6,6-trimethyl-1-cyclohexane-1-methanol prepared according to Example XVII is added to half of the above formulation at the rate of 0.2%. The formulation with the α-isopropenyl-2,6,6-trimethyl-1-cyclohexene-1-methanol is compared with the formulation without the α-isopropenyl-2,6,6-trimethyl-1-cyclohexene-1-methanol at the rate of 0.01% (100 ppm) in water and evaluated by a bench panel.

The flavor containing the α-isopropenyl-2,6,6-trimethyl-1-cyclohexene-1-methanol is found to have a substantially more pleasant and better raspberry aroma. It is the unanimous opinion of the bench panel that the chemical, α-isopropenyl-2,6,6-trimethyl-1-cyclohexene-1-methanol rounds the flavor out and contributes to a very natural fresh aroma and taste as found in full ripe raspberries. Accordingly, the flavor with the addition of the α-isopropenyl-2,6,6-trimethyl-1-cyclohexene-1-methanol is considered as substantially better than the flavor without α-isopropenyl-2,6,6-trimethyl-1-cyclohexene-1-methanol.

EXAMPLE XXIX

Tobacco Formulation

A tobacco mixture is produced by admixing the following ingredients:

| Ingredients | Parts by Weight |
|---|---|
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco.

The following flavor formulation is prepared:

| Ingredients | Parts by Weight |
|---|---|
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above-stated tobacco flavor formulation is applied at the rate of 1.0% to all of the cigarettes produced using the above tobacco formulation. Half of the cigarettes are then treated with 500 or 1,000 ppm of the compound produced according to Example XVII, the α-isopropenyl-2,6,6-trimethyl-1-cyclohexene-1-methanol. The control cigarettes not containing the α-isopropenyl-2,6,6-trimethyl-1-cyclohexene-1-methanol produced according to the process of Example XVII and the experimental cigarettes which contain the α-isopropenyl-2,6,6-trimethyl-1-cyclohexene-1-methanol produced according to Example XVII are evaluated by paired comparison and the results are as follows:

The experimental cigarettes are found to have more body in tobacco smoke flavor and a fuller body sensation. The oriental, tobacco-like notes are enhanced and the flavor of the tobacco on smoking is more aromatic with floral, oriental, sweet and fruity aroma and taste nuances.

The tobacco smoke flavor of the experimental cigarettes has floral, woody, oriental, sweet and fruity notes. All cigarettes are evaluated for smoke flavor with a 20 mm cellulose acetate filter.

EXAMPLE XXX

Raspberry Flavor Formulation

| Ingredient | Parts by Weight |
|---|---|
| Vanillin | 2.0 |
| Maltol | 5.0 |
| Parahydroxybenzylacetone | 5.0 |
| Alpha-ionone (10% in Propylene glycol) | 2.0 |
| Ethyl butyrate | 6.0 |
| Ethyl acetate | 16.0 |
| Dimethyl sulfide | 1.0 |
| Isobutyl acetate | 13.0 |
| Acetic acid | 10.0 |
| Acetaldehyde | 10.0 |
| Propylene glycol | 930.0 |
| TOTAL | 1000.0 |

α-Isopropenyl-2,6,6-trimethyl-1,3-cyclohexadiene-1-methanol having the structure:

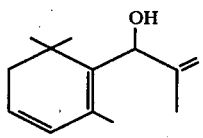

prepared according to Example I is added to half of the above formulation at the rate of 0.2%. The formulation with the α-isopropenyl-2,6,6-trimethyl-1,3-cyclohexadiene-1-methanol is compared with the formulation without the α-isopropenyl-2,6,6-trimethyl-1,3-cyclohexadiene-1-methanol at the rate of 0.01% (100 ppm) in water and evaluated by a bench panel.

The flavor containing the α-isopropenyl-2,6,6-trimethyl-1,3-cyclohexadiene-1-methanol having the structure:

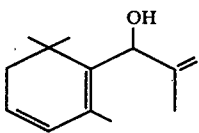

is found to have a substantially more pleasant and better raspberry juice aroma and taste. It also has the sweet, grapejuice-like nuances so desired in fruit flavors. It is the unanimous opinion of the bench panel that the α-isopropenyl-2,6,6-trimethyl-1,3-cyclohexadiene-1-methanol rounds the flavor out and contributes to a very natural, fresh aroma and taste found in full, ripe raspberries and, in addition, has the very interesting and useful grape nuance. Accordingly, the flavor with the addition of the α-isopropenyl-2,6,6-trimethyl-1,3-cyclohexadiene-1-methanol is considered as substantially better than the flavor without said α-isopropenyl-2,6,6-trimethyl-1,3-cyclohexadiene-1-methanol.

EXAMPLE XXXI

Raspberry Flavor Formulation

The following basic raspberry flavor formulation is produced:

| Ingredient | Parts by Weight |
|---|---|
| Vanillin | 2.0 |
| Maltol | 5.0 |
| Parahydroxybenzylacetone | 5.0 |
| Alpha-ionone (10% in Propylene glycol) | 2.0 |
| Ethyl butyrate | 6.0 |
| Ethyl acetate | 16.0 |
| Dimethyl sulfide | 1.0 |
| Isobutyl acetate | 13.0 |
| Acetic acid | 10.0 |
| Acetaldehyde | 10.0 |
| Propylene glycol | 930.0 |
| TOTAL | 1000.0 |

α(1-cis-n-propenyl)-2,6,6-trimethyl-1,3-cyclohexadiene-1-methanol produced according to Example XI is added to half of the above formulation at the rate of 0.2%. The formulation with the α(1-cis-n-propenyl)-2,6,6-trimethyl-1,3-cyclohexadiene-1-methanol is compared with the formulation without the α(1-cis-n-propenyl)-2,6,6-trimethyl-1,3-cyclohexadiene-1-methanol at the rate of 0.01% (100 ppm) in water and evaluated by a bench panel.

The flavor containing the α(1-cis-n-propenyl)-2,6,6-trimethyl-1,3-cyclohexadiene-1-methanol is found to have a substantially more pleasant and better raspberry aroma. It is the unanimous opinion of the bench panel that the chemical α(1-cis-n-propenyl)-2,6,6-trimethyl-1,3-cyclohexadiene-1-methanol rounds the flavor out and contributes to a very natural fresh aroma and taste as found in full ripe raspberries. Accordingly, the flavor with the addition of the α(1-cis-n-propenyl)-2,6,6-trimethyl-1,3-cyclohexadiene-1-methanol is considered as substantially better than the flavor without α(1-cis-n-propenyl)-2,6,6-trimethyl-1,3-cyclohexadiene-1-methanol.

EXAMPLE XXXII

Tobacco Formulation

A tobacco mixture is produced by admixing the following ingredients:

| Ingredients | Parts by Weight |
|---|---|
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco.

The following flavor formulation is prepared:

| Ingredients | Parts by Weight |
|---|---|
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |

| Ingredients | Parts by Weight |
| --- | --- |
| Water | 41.90 |

The above-stated tobacco flavor formulation is applied at the rate of 1.0% to all of the cigarettes produced using the above tobacco formulation. Half of the cigarettes are then treated with 500 or 1,000 ppm of the product produced according to Example XI; α(1-cis-n-propenyl)-2,6,6-trimethyl-1,3-cyclohexadiene-1-methanol. The control cigarettes not containing the α(1-cis-n-propenyl)-2,6,6-trimethyl-1,3-cyclohexadiene-1-methanol produced according to the process of Example XI and the experimental cigarettes which contain the α(1-cis-n-propenyl)-2,6,6-trimethyl-1,3-cyclohexadiene-1-methanol produced according to Example XI are evaluated by paired comparison and the results are as follows:

The experimental cigarettes are found to have more body in tobacco smoke flavor and a fuller body sensation. The tobacco-like notes are enhanced and the flavor of the tobacco on smoking is more aromatic with floral, musty, hay-tea-like, sweet and fruity aroma and taste nuances.

The tobacco smoke flavor of the experimental cigarettes has floral, musty, hay-tea-like, sweet and fruity notes. All cigarettes are evaluated for smoke flavor with a 20 mm cellulose acetate filter.

EXAMPLE XXXIII

Raspberry Flavor Formulation

The following basic raspberry flavor formulation is produced:

| Ingredient | Parts by Weight |
| --- | --- |
| Vanillin | 2.0 |
| Maltol | 5.0 |
| Parahydroxybenzylacetone | 5.0 |
| Alpha-ionone (10% in Propylene glycol) | 2.0 |
| Ethyl butyrate | 6.0 |
| Ethyl acetate | 16.0 |
| Dimethyl sulfide | 1.0 |
| Isobutyl acetate | 13.0 |
| Acetic acid | 10.0 |
| Acetaldehyde | 10.0 |
| Propylene glycol | 930.0 |
| TOTAL | 1000.0 |

α(1-trans-n-propenyl)-2,6,6-trimethyl-1,3-cyclohexadiene-1-methanol produced according to Example XI is added to half of the above formulation at the rate of 0.2%. The formulation with the α(1-trans-n-propenyl)-2,6,6-trimethyl-1,3-cyclohexadiene-1-methanol is compared with the formulation without the α(1-trans-n-propenyl)-2,6,6-trimethyl-1,3-cyclohexadiene-1-methanol at the rate of 0.01% (100 ppm) in water and evaluated by a bench panel.

The flavor containing the α(1-trans-n-propenyl)-2,6,6-trimethyl-1,3-cyclohexadiene-1-methanol is found to have a substantially more pleasant and better raspberry aroma. It is the unanimous opinion of the bench panel that the chemical α(1-trans-n-propenyl)-2,6,6-trimethyl-1,3-cyclohexadiene-1-methanol rounds the flavor out and contributes to a very natural fresh aroma and taste as found in full ripe raspberries. Accordingly, the flavor with the addition of the α(1-trans-n-propenyl)-2,6,6-trimethyl-1,3-cyclohexadiene-1-methanol is considered as substantially better than the flavor without α(1-trans-n-propenyl)-2,6,6-trimethyl-1,3-cyclohexadiene-1-methanol.

EXAMPLE XXXIV

Tobacco Formulation

A tobacco mixture is produced by admixing the following ingredients:

| Ingredients | Parts by Weight |
| --- | --- |
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco.

The following flavor formulation is prepared:

| Ingredients | Parts by Weight |
| --- | --- |
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above-stated tobacco flavor formulation is applied at the rate of 1.0% to all of the cigarettes produced using the above tobacco formulation. Half of the cigarettes are then treated with 500 or 1,000 ppm of the compound produced according to Example XI; α(1-trans-n-propenyl)-2,6,6-trimethyl-1,3-cyclohexadiene-1-methanol. The control cigarettes not containing the α(1-trans-n-propenyl)-2,6,6-trimethyl-1,3-cyclohexadiene-1-methanol produced according to the process of Example XI and the experimental cigarettes which contain the α(1-trans-n-propenyl)-2,6,6-trimethyl-1,3-cyclohexadiene-1-methanol produced according to Example XI are evaluated by paired comparison and the results are as follows:

The experimental cigarettes are found to have more body in tobacco smoke flavor and a fuller body sensation. The tobacco-like notes are enhanced and the flavor of the tobacco on smoking is more aromatic with floral, musty, hay-tea-like, sweet and fruity aroma and taste nuances.

The tobacco smoke flavor of the experimental cigarettes has floral, musty, hay-tea-like, sweet and fruity notes. All cigarettes are evaluated for smoke flavor with a 20 mm cellulose acetate filter.

EXAMPLE XXXV

SYNTHESIS OF 2,6,6-TRIMETHYL-ALPHA-n-PROPENYL-1,3-CYCLOHEXADIENE-1-METHANOL

Reaction:

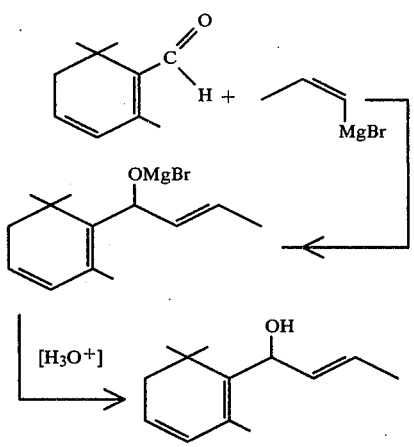

A one liter 3-neck reaction flask equipped with mechanical stirrer, water cooled condenser, immersion thermometer and 250 ml addition funnel is set up and allowed to dry over night under a nitrogen atmosphere. 24 Grams (1.0 moles) of magnesium shavings previously washed with 3 volumes of diethylether is added to the reaction flask with 200 ml of anhydrous tetrahydrofuran. 100 Grams (0.83 moles) of 1-bromo-1-propene (50:50 cis:trans isomer mixture) dissolved in 150 ml tetrahydrofuran is added dropwise using the cooling bath and addition rate to keep a temperature in the reaction vessel of 30°–35° C. The temperature is then allowed to rise to 45° C. in order to instigate reaction. The reaction mixture is then stirred at 25°–30° C. for an additional 30 minutes under nitrogen. Safranal (80 gms./0.54 moles) (2,6,6-trimethyl-1,3-cyclohexadiene-1-carboxaldehyde) is dissolved in 100 ml anhydrous tetrahydrofuran and added dropwise under nitrogen to the reaction mixture while maintaining the reaction mixture at 25°–30° C. After addition of the safranal, the reaction mass is stirred for a period of one hour. The nitrogen blanket is then stopped and approximately 50 ml of saturated ammonium chloride solution is added dropwise keeping the reaction mass temperature at 25°–30° C. The reaction mass is then filtered under water vacuum and washed with diethyl ether. The resulting extract is concentrated on a "rotovap" in order to remove the tetrahydrofuran. The resulting residue is then taken up between diethyl ether and saturated sodium chloride solution and washed with two volumes of saturated sodium chloride solution; and then dried and concentrated to yield 112.06 grams of a crude material. The GLC profile for this crude material indicates a highly complex mixture. A 0.1 micro liter injection was made on a 400'×0.032" SE 30 GLC column (conditions: temperature programmed from 70° C.–180° C. at 3° C. per minute; equipment Varian 3700 equipped with flame ionizing detector, injection temperature 250° C.; detector temperature 250° C.; flow rate (helium carrier gas) −10 ml/minute). Subsequent analysis indicates a peak in a GLC profile to be a compound having one or both of the structures:

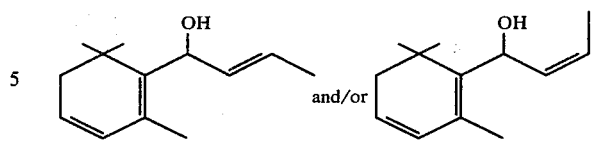

A preliminary silica gel column (denoted as "a") (200 grams of 5% H2O deactivated SiO2) is set up and approximately 10 grams of the crude material is put on it with 10% diethyl ether and eluted as follows:

| Fraction # | Solvent    | Volume |
|------------|------------|--------|
| 1–4a       | 10% ether  | 4 oz.  |
| 5–10a      | 15% ether  | 4 oz.  |
| 11–13a     | 50%        | 4 oz.  |

Fraction 7a is found to be greater than 90% compound having the structure:

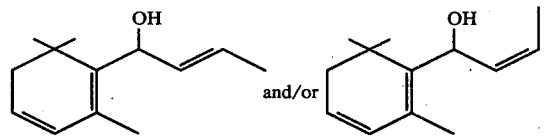

A second column (denoted as "b") is then set up using 700 gms. of silica gel—5% water placing approximately 40 grams of crude thereon and eluting as follows:

| Fraction # | Solvent    | Volume |
|------------|------------|--------|
| 1–4b       | 10% ether  | 250 ml |
| 5–7b       | 15% ether  | 250 ml |
| 8–10b      | 20% ether  | 250 ml |
| 11–12b     | 50% ether  | 250 ml |
| 13–14b     | 100% ether | 250 ml |

Fractions 7–9b are found to contain (a) compound(s) having one or both of the structures:

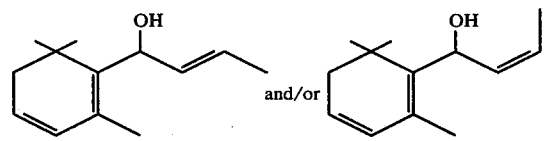

and are bulked with fractions 6–8a (from column "a") to yield 5.30 grams of a crude 2,6,6-trimethyl-α-n-propenyl-1,3-cyclohexadiene-1-methanol. Fractions 7–9b taken together with fractions 6–8a are set up for further chromatography. Fractions 6–8a and 7–9b are placed in bulked form on 200 grams of 5% H2O-deactivated silica gel with 10% diethyl ether in isopentane. The chromatography column is washed with 10% diether ether until odor free. Then ninety-five (95) 15 ml fractions are collected (eluted with 10% diethyl ether) and air concentrated. Every tenth fraction from fraction 10 to fraction 40 is subjected to GLC analysis. Bulking is done as follows:

Fractions 3–23: 23.1% 2,6,6-trimethyl-α-n-propenyl-1,3-cyclohexadiene-1-methanol and 3.5% safranal;

Fractions 24–37: 92.2%, 2,6,6-trimethyl-α-n-propenyl-1,3-cyclohexadiene-1-methanol and 0.6% safranal;

Fractions 38–95: 96.4% 2,6,6-trimethyl-α-n-propenyl-1,3-cyclohexadiene-1-methanol and 0% safranal.

What is claimed is:

1. A process for augmenting or enhancing the aroma or taste of a foodstuff comprising adding thereto from about 0.05 parts per million up to about 100 parts per million based on the total composition of a substance selected from the group consisting of:

(a) a mixture of compounds having the structures:

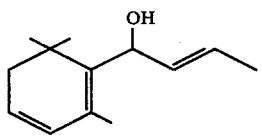

and

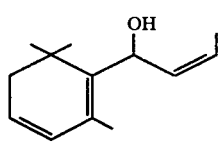

(b) a compound having the structure:

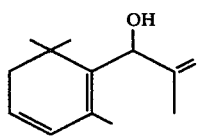

2. A composition for augmenting or enhancing the aroma or taste of a foodstuff comprising (i) from about 0.1% up to about 15% by weight based on the total weight of said flavoring composition of a substance selected from the group consisting of:

(a) a mixture of compounds having the structures:

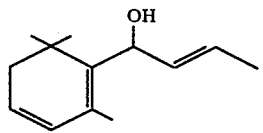

and

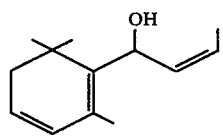

(b) a compound having the structure:

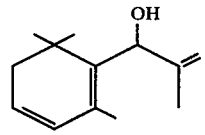

and (ii) the remainder of said composition being at least one flavor adjuvant selected from the group consisting of:

p-Hydroxybenzyl acetone;
Geraniol;
Cassia Oil;
Acetaldehyde;
Maltol;
Ethyl methyl phenyl glycidate;
Benzyl acetate;
Dimethyl sulfide;
Eugenol;
Vanillin;
Caryophyllene;
Methyl cinnamate;
Guiacol;
Ethyl pelargonate;
Cinnamaldehyde;
Methyl anthranilate;
5-Methyl furfural;
Isoamyl acetate;
Isobutyl acetate;
Cuminaldehyde;
Alpha ionone;
Cinnamyl formate;
Ethyl butyrate;
Methyl cinnamate;
Acetic acid;
Gamma-undecalactone;
Naphthyl ethyl ether;
Diacetyl;
Furfural;
Ethyl acetate;
Anethole;
2,3-Dimethyl pyrazine;
2-Ethyl-3-methyl pyrazine;
3-Phenyl-4-pentenal;
2-Phenyl-2-hexenal;
2-Phenyl-2-pentenal;
3-Phenyl-4-pentenal diethyl acetal;
1-Crotonyl-2,2,6-trimethylcyclohex 1-ene;
1-Crotonyl-2,2,6-trimethylcyclohexa-1,3-diene;
α-Damascone;
δ-Damascone;
2,2,6-trimethyl-cyclohex-1-ene carboxaldehyde);
Isoamyl butyrate;
Cis-3-hexenol-1;
2-Methyl-2-pentenoic acid;
2-Methyl-cis-3-pentenoic acid;
2-Methyl-cis-3-pentenoic acid ethyl ester;
4-Allyl-1,2,6-trimethoxy-benzene;
4-Propenyl-1,2,6-trimethoxy-benzene; and
2-(4-Hydroxy-4-methylpentyl) norbornadiene.

* * * * *